(12) United States Patent
Williams et al.

(10) Patent No.: US 7,208,480 B2
(45) Date of Patent: Apr. 24, 2007

(54) POLYSACCHARIDE BASED GEL

(75) Inventors: Peter Williams, Wrexham (GB);
Martina Hickey, Wrexham (GB);
David Mitchell, Harrow (GB)

(73) Assignee: Chesham Chemicals Limited, Middlesex (GB)

( * ) Notice: Subject to any disclaimer, the term of this patent is extended or adjusted under 35 U.S.C. 154(b) by 0 days.

(21) Appl. No.: 10/311,383

(22) PCT Filed: Jun. 15, 2001

(86) PCT No.: PCT/GB01/02637

§ 371 (c)(1),
(2), (4) Date: Feb. 11, 2003

(87) PCT Pub. No.: WO01/96461

PCT Pub. Date: Dec. 20, 2001

(65) Prior Publication Data
US 2004/0131645 A1    Jul. 8, 2004

(30) Foreign Application Priority Data
Jun. 16, 2000 (GB) .................. 0014865.0

(51) Int. Cl.
*A61K 31/736* (2006.01)
(52) U.S. Cl. .................. 514/54; 424/434; 424/439; 424/488; 424/500; 426/573
(58) Field of Classification Search ........... 424/195.18, 424/70.1, 401; 514/782, 780
See application file for complete search history.

(56) References Cited

U.S. PATENT DOCUMENTS

| 3,557,016 A | 1/1971 | Schuppner |
| 3,804,951 A | 4/1974 | Rapp et al. |
| 4,676,976 A | 6/1987 | Toba et al. |
| 6,537,318 B1 * | 3/2003 | Ita et al. ............ 623/11.11 |
| 6,719,967 B1 * | 4/2004 | Brown et al. ........... 424/70.1 |

FOREIGN PATENT DOCUMENTS

| EP | 0602990 A1 | 6/1994 |
| WO | 97/18263 | 5/1997 |

OTHER PUBLICATIONS

Goycoolea, F., "Screening for synergistic interactions in dilute polysaccharide solutions", Carbohydrate Polymers 28 (1995) 351-358, pp. 351-358.*
Rinaudo et al.; "Physical Properties of Xanthan, Galactomannan and Their Mixtures in Aqueous Solutions"; *Macromolecular Symposia*; vol. 140, May 1999; pp. 115-124 (XP000866710).

* cited by examiner

*Primary Examiner*—Sreeni Padmanabhan
*Assistant Examiner*—Gina C. Yu
(74) *Attorney, Agent, or Firm*—Nixon & Vanderhye P.C.

(57) ABSTRACT

A fluid gel obtainable by a process which comprises subjecting a solution comprising a mixture of xanthan and one or more non-gelling polysaccharides selected from galactomannans or glucomannans in a solvent to shear while cooling the solution from a temperature above the gelation temperature of the mixture, and recovering the resulting continuous gel. The gel is useful in cosmetic and pharmaceutical compositions where it may, for instance, be generated in situ.

24 Claims, 2 Drawing Sheets

POLYSACCHARIDE BASED GEL

The present invention relates to fluid gels of xanthan and non-gelling polysaccharides and processes for producing these fluid gels. The invention also relates to compositions comprising the fluid gels and uses of the gels and of the compositions.

There is a growing desire in the cosmetics industry to move away from the use of synthetic materials in gels and to use natural polymers such as polysaccharides instead. However, the gels formed from such polysaccharides tend to be rigid and consequently of limited use in cosmetic applications.

The present invention provides a fluid gel obtainable by a process which comprises subjecting a solution comprising a mixture of xanthan and one or more non-gelling polysaccharides selected from galactomannans and glucomannans in a solvent to shear while cooling the solution from a temperature above the gelation temperature of the mixture, and recovering the resulting continuous gel.

The gels of the present invention comprise xanthan and one or more non-gelling polysaccharides chosen from galactomannans and glucomannans. Examples of non-gelling polysaccharides include konjac mannan, tara, locust bean and guar gums. In a preferred embodiment of the present invention the gel comprises a mixture of xanthan and locust bean gum (lbg) or konjac mannan (km). In a particularly preferred embodiment the gel comprises a mixture of xanthan and konjac mannan.

Modified xanthan or a modified non-gelling polysaccharide may be used in the present invention. Modification may be, for example, by depolymerisation, chemical action or enzymatic action. Examples of modified products are depolymerised locust bean gum and enzyme modified guar gum.

Xanthan is an anionic bacterial polysaccharide whose commercial source is the bacterium *Xanthomonas campestris*. Xanthan is produced commercially by aerobic fermentation of this bacterium in batch culture. Precipitation with alcohol enables xanthan to be isolated from the culture broth. On removing the bacterial cells prior to alcohol precipitation a clarified product can be produced. Xanthan gum typically takes the form of an off-white powder with a moisture content of approximately 11% and an ash content of 6–9%. The viscosity of a xanthan solution is relatively insensitive to pH.

The viscosity of polysaccharide solutions normally decreases on addition of an electrolyte. However, for xanthan solutions of concentrations greater than 0.15% the electrolyte has the opposite effect and increases the viscosity. This is due to the electrolyte promoting helix formation. It is reported that maximum viscosity is obtained at a concentration of 0.02–0.07% sodium chloride. Addition of salt above this concentration has little or no effect on viscosity or stability. Addition of di- or trivalent cations also enhances the thixotropy of xanthan solutions.

The viscosity of aqueous xanthan solutions over a broad temperature range is almost constant. It has been shown that in the presence of salt, i.e. 0.1% concentration sodium chloride, the viscosity of xanthan solutions is practically unaffected by temperatures ranging from 4 to 93° C. This is contrary to most other polysaccharide solutions for which, on heating, the viscosity decreases.

Locust bean gum (lbg) is the refined endosperm of the seed of the carob tree known botanically as *Ceretonia siliqua*. The endosperm is separated from the husk and the germ of the seed by the process known as oven dehulling. This involves the seeds being heated to high temperatures for approximately 45 seconds and then being passed through a series of roller mills which enable the husk and germ to be removed simultaneously. It is important that complete removal of the husk is achieved during endosperm separation, otherwise specks may be observed in the gum which may cause loss in viscosity over time in prepared gum solutions.

Konjac mannan (km) is a linear polysaccharide derived from the konjac tuber of the amorphophallus species found in east Asia, from which a glucomannan flour may be obtained after subsequent drying and milling of the tuber. The polysaccharide has been used for many years as a food component in India, Pakistan and Japan. Konjac mannan is water soluble and produces highly viscous solutions which exhibit pseudoplastic flow.

The xanthan and non-gelling polysaccharides may be present in the fluid gel of the present invention in equal or unequal amounts. Where the gel comprises xanthan and one non-gelling polysaccharide these two components are typically present in a weight ratio of from 1:10 to 10:1, preferably 9:1 to 1:1.

The gels of the present invention are fluid. Depending on the concentration of the solution and the choice of non-gelling polysaccharides, the gels range in viscosity from pourable to spreadable gels. Gels formed from solutions of a lower concentration are generally pourable and gels formed from solutions of a higher concentration are generally spreadable. Pourable gels may typically be formed from solutions of 0.1% by weight of polysaccharide or lower.

In one embodiment the gels of the present invention are spreadable. The term "spreadable" means that the gel flows at low strain; for example, it can be spread easily by rubbing (possibly into the skin). When it flows the gel has a very smooth consistency. The gel flow proceeds smoothly at low strain and is different from the fracturing observed when a rigid gel is subjected to strain. The fluid (for instance spreadable) gels of the present invention, being formed by a process which includes a shearing step, are substantially less rigid than non-sheared gels. The gels are also noted for their good 'skin feel'. When applied to the skin, the gels rub in well and do not leave the skin feeling tight or sticky.

Gels are typically characterised by their rheological properties such as the storage (G') and loss (G") moduli. The (stronger and) more rigid a gel is, the higher the value of G'. The value of G" is generally lower than the value of G'.

G' and G" are measured in the linear viscoelastic region where stress is linearly proportional to strain.

The gels of the present invention are fluid and have a lower value of G' than gels formed under non-sheared conditions. It is thought that the shear applied as gelation is occurring serves to disrupt the gel structure, thereby inhibiting the formation of a complete interpenetrating three dimensional network and thus forming slightly weaker and softer gels.

The present invention also provides a process for producing a fluid gel, which process comprises subjecting a solution comprising a mixture of xanthan and one or more non-gelling polysaccharides chosen from galactomannans and glucomannans in a solvent to shear while cooling the solution from a temperature above the gelation temperature of the mixture, and recovering the resulting continuous gel.

It is an essential part of the process that the gel is subjected to shear as it cools through the gelation temperature. By subjecting to shear is to be understood subjecting to any suitable form of agitation which results in a fluid gel. For example, the solution may be sheared, stirred, shaken, disrupted, homogenised or agitated in any other way such as using ultrasound. Shearing may be conducted at a constant rate, i.e. controlled shearing, for instance in a Rheometer. Shearing may also be conducted at a non-constant rate, i.e. non-controlled shearing, for instance with a mechanical stirrer. Any suitable rate of shearing may be used.

Applying shear to the xanthan-lbg and xanthan-km systems while gelation occurs leads to the formation of soft, fluid continuous gels. These are different from other sheared gels, such as those described in EP-A-0 355 908 and EP-A-0 432 835 which are described as being particulate and do not tend to be fluid and continuous. The rheological profiles of the sheared gels of the present invention thus differ from those of non-sheared gels.

Typically, the shearing takes place while the solution cools from above the gelation temperature of the mixture of constituent polysaccharides, typically to room temperature. Normally the cooling takes place naturally, that is the gel cools gradually to room temperature. However either natural cooling or quench cooling may be used. Any manner of cooling which results in a fluid gel may be used. The solution may also be alternately quench cooled and naturally cooled when appropriate.

The shearing and cooling are typically simultaneous. Shearing may be conducted throughout the entire cooling process, or only during cooling through the gelation temperature. Shearing and cooling may take place contemporaneously or sequentially, for instance as alternating steps. For example, the solution may be sheared while being held at a constant temperature and then allowed to cool, followed by furer shearing at a lower constant temperature and subsequent cooling. However, it is essential that shearing takes place as the solution gels, that is as the solution cools through the gelation temperature.

The xanthan and non-gelling polysaccharide solution generally comprises from 0.01 to 5% by weight of xanthan and non-gelling polysaccharide, typically from 0.05 to 2% and often 1%. A typical solution is produced by dissolving dried xanthan and non-gelling polysaccharide in distilled water such that the final polymer concentration is from 0.05 to 5%. Particularly preferred are solutions of 0.1–1% concentration. The preferred concentration for any particular combination of xanthan and polysaccharide depends on the non-gelling polysaccharide(s) chosen.

The solutions of xanthan and other non-gelling polysaccharides used in the present invention are typically aqueous solutions. Generally the dried xanthan and non-gelling polysaccharide(s) are dissolved in distilled water and then heated. However, solutions may be formed from other solvents or solvent mixtures. Examples of other solvents which are suitable include alcohols such as methanol, ethanol, isopropanol, cetyl alcohol, stearyl alcohol and glycols, ketones such as acetone and benzophenone and acetates. These solvents may be used alone, as mixtures with each other or mixed with water.

The solution is typically heated to above the gelation temperature of the mixture of xanthan and said one or more non-gelling polysaccharides. The solution is therefore typically heated to above 50° C. and generally to above 70° C., for example 80° C. However, the solution may be heated to above 90° C.

The solution is then allowed to cool to below the said gelation temperature. The gelation temperature may be defined as the temperature at which G' increases markedly. Typically the solution is allowed to cool to room temperature which is from 15 to 30° C., more preferably from 18 to 24° C.

The viscosity of the resulting gel is partly dependent on the temperature to which the starting xanthan and non-gelling polysaccharide solution is heated prior to cooling and shearing. For instance, the viscosity of a xanthan-konjac mannan gel which results from heating the starting solution to 90° C. is generally higher than the viscosity of a corresponding gel which results from heating the starting solution to 70° C. or 50° C. The properties of a gel of the invention may thus be changed by appropriate modification of the temperature to which the starting polysaccharide solution is heated. However, other factors such as the addition of electrolyte can also affect the properties of the gel.

The xanthan and polysaccharide(s) are typically mixed as dry powders and then dissolved in solvents. However, making each constituent component of the gel of the invention as a separate solution and mixing the said solutions is also an embodiment of the present invention. The solutions may be mixed before or after heating to above the gelation temperature. For example the solutions may be mixed before heating, or after heating but before cooling to below the gelation temperature. The two (or more) solutions must come into contact before gelation occurs.

The gels of the present invention may be combined with other ingredients to form compositions, for instance cosmetic or pharmaceutical compositions for application to the skin. Examples of such compositions include creams, gels and lotions. They may also be used in toiletries including shampoos, deodorants, antiperspirants and toothpaste, in pharmaceutical compositions for application in the buccal cavity or to skin, in foods for animals or humans, for example confectionery, and in other materials such as agrochemicals, paints and inks. The compositions typically comprise a fluid gel of the present invention and a physiologically tolerable carrier, adjuvant or diluent. The composition may also comprise a pigment, a pharmaceutically active compound, a sunscreen active compound, a silicone or derivative thereof, an inorganic salt, a further solvent or a perfume.

Suitable ingredients for use in compositions comprising a gel of the present invention include 1,3-butylene glycol, acetaminophen, acetylated lanolin alcohol, acrylates copolymer, alpha olefin sulfonate, alumnina, ammuonium lauryl sulfate, butylated hydroxytoluene, caprylic/capric tryiglcerides, carbomer, carbomer 940, carbomer 941, carboxymethyl cellulose, cellulose gum, centrimonium chloride, ceresin, cetearyl alcohol, cetearyl isononanoate, cetearyl octanoate, cetyl acetate, cetyl alcohol, cetyl dimethicone copolyol, cetyl trinethyl ammonium chloride, cholesterol, citric acid, cocamide DEA, cocamide MEA, cocamidopropyl betaine, cocoamphocarboxypropionate, coconut oil diethanolamine condensate, dicaprylyl maleate, diethanolamine, diinethicone, dipropylene glycol, disodium pareth-3 sulfosuccinate, ethanol, ethylene glycol monostearate, fatty acid ester, glycerin, glycerol monostearate (and) polyoxyethylene, glyceryl monostearate, glyceryl oleate, glyceryl stearate, glycol disterate, hexylene glycol, hydrated silica, hydroxyethyl cellulose, hydroxypropyl guar hydroxypropyltrimonium chloride, isopropyl palitate, kaolin, lactic acid, laneth-10 acetate, laneth-16, lanolin, lanolin alcohol, lanolin oil, lauramide DEA, laureth-3, lauric acid, lauric fatty acids, lauroamphodiacetate, lauroyl sarcosine, magnesium aluminium silicate, magesium stearate, magnesium sulphate, methyl gluceth-10 ethoxylated, methyl gluceth-20, mica, microcrystalline cellulose, mineral oil, oleamide MIPA, oleic acid, oleth-3 phosphate, oleyl alcohol, paraffinium liquidum, PEG-18 glyceryl oleate/cocoate, PEG-20 stearate, PEG-40 castor oil, PEG-40 hydrogenated castor oil, PEG-6 Cocamide, PEG-7 glyceryl cocoate, petrolatum, pigments, polyethylene, polyoxypropylene 15 stearyl ether, polyquaternium-7, polysorbate 20, polysorbate 60, polysorbate 80, potassium acesulfame, potassium hydroxide, propylene glycol, silica, sodium aluminium chlorhydroxylactate, sodium chloride, sodium citrate, sodium fluoride, sodium hydroxide, sodium laureth sulfate, sodium lauroyl sarcosinate, sodium lauryl sulfate, sodium monofluorophosphate, sodium N-methyl-N-myristoyl-taurate, sodium saccharin, sorbitan isostearate, sorbitan monopahlmtate fatty acid ester, sorbitol, stearamidopropyl dimethylamine, stearate fatty acid ester, steareth-2, steareth-21, stearic acid, stearyl alcohol, stearyl alcohol (and) ceteareth-20 condensate, synthetic beeswax, talc, tetrasodium EDTA, theobromo cacao, titanium dioxide, titanium dioxide MT100T, triclosan, triethanolamine, xanthan gum, zinc oxide (Nanox) and zinc pyrithione (dispersion).

The further solvent may be an organic solvent with a low boiling point, for example, an ether which could not be added until after the solution has cooled. However, any suitable organic solvent may be added to the composition after cooling.

In a further embodiment of the invention, other components of the final composition may be added to the solution before shearing takes place. These may be added at any suitable temperature. For example, certain solvents and perfumes are typically added at low temperatures in order not to vaporise, whereas inorganic salts may be added at any temperature.

In one embodiment of the present invention the gel of the present invention is formed in situ in the composition. In this embodiment the gel components are typically provided in a dry form, e.g. as powder, and the composition is subjected to shear after the gel components have been added. Further components may be added after the shearing step has taken place. Accordingly, the invention farther provides a cosmetic or pharmaceutical composition obtainable by a process which comprises:
  (a) forming an aqueous phase comprising one or more cosmetically or pharmaceutically acceptable carriers, adjuvants or diluents and a mixture of xanthan and one or more non-gelling polysaccharides selected from galactomannans and glucomannans;
  (b) Subjecting the aqueous phase to shear while cooling it from a temperature above the gelation temperature of the said mixture; and
  (c) recovering the resulting cosmetic or pharmaceutical composition.

The invention also provides a process for producing a cosmetic or pharmaceutical composition which process comprises:
  (a) forming an aqueous phase comprising one or more cosmetically or pharmaceutically acceptable carriers, adjuvants or diluents and a mixture of xanthan and one or more non-gelling polysaccharides selected from galactomannans and glucomannans;
  (b) Subjecting the aqueous phase to shear while cooling it from a temperature above the gelation temperature of the said mixture; and
  (c) recovering the resulting cosmetic or pharmaceutical composition.

A composition of the present invention may be formulated to be a topical, oral or mucosal contact gel or lotion.

The spreadable gels of the present invention are typically optically clear. The gels can therefore be used in many therapeutic and/or diagnostic techniques. For example, they are suitable for use in ultrasound or ECG tests.

The invention is further described in the Examples which follow, with reference to the accompanying drawings, in which xanthan, locust bean gum and konjac mannan were all obtained from commercial sources. G' and G" were measured using a Carrimed CSL$^2$500 controlled stress rheometer (TA Instruments, UK).

DRAWINGS

EXAMPLE 1

Figure 1:
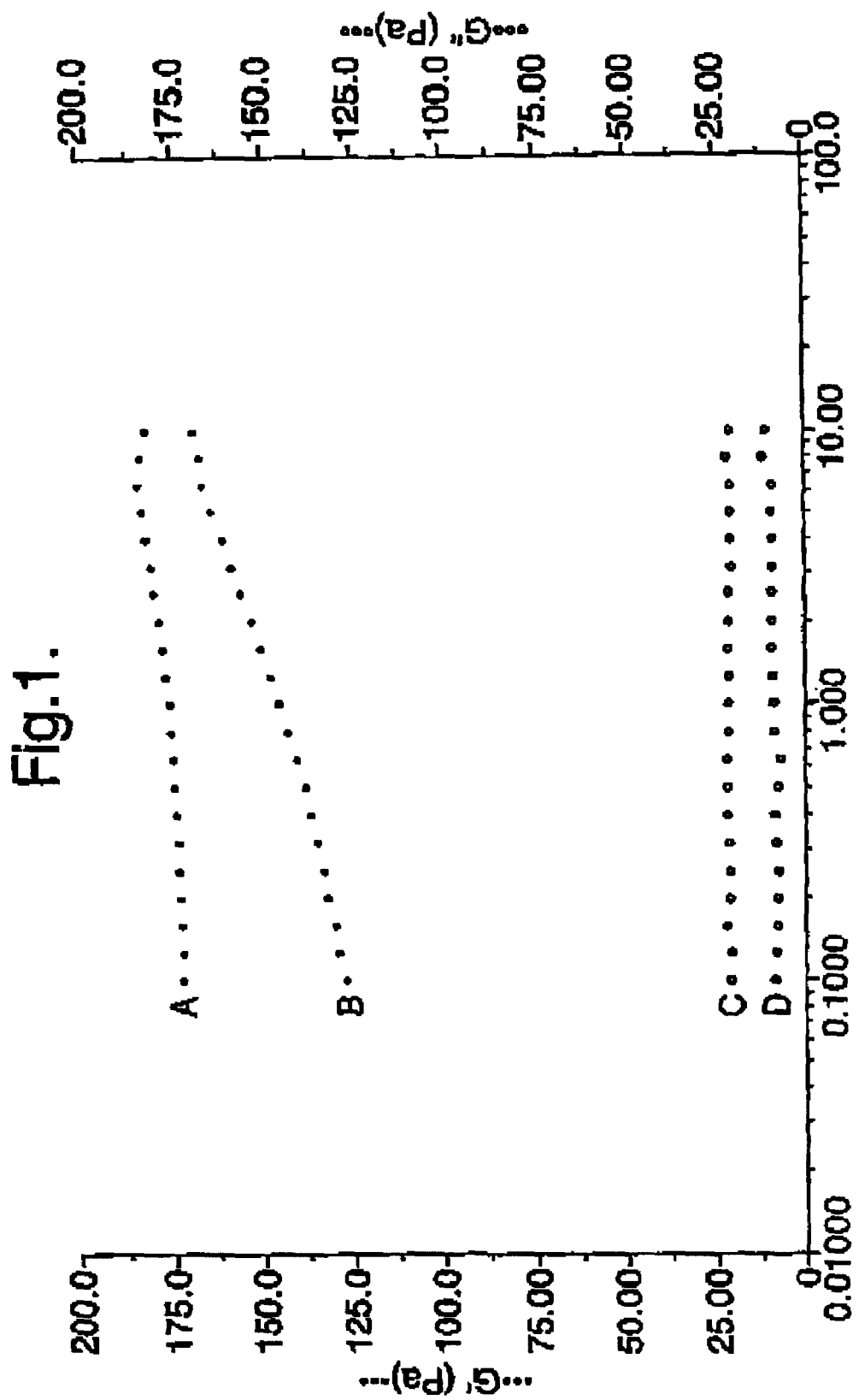
FIG. 1 shows a comparison of G' and G" (y axis) for sheared and non-sheared xanthan-konjac mannan gels of 0.5% concerntration at 25° C. in water over a frequency range of 0.1 to 10 Hertz (Hz) (x axis). Plot A relates to G' for non-sheared gels, plot B to G' sheared gels, plot C to G" for sheared gels and plot D to G" for non-sheared gels.
Figure 2:
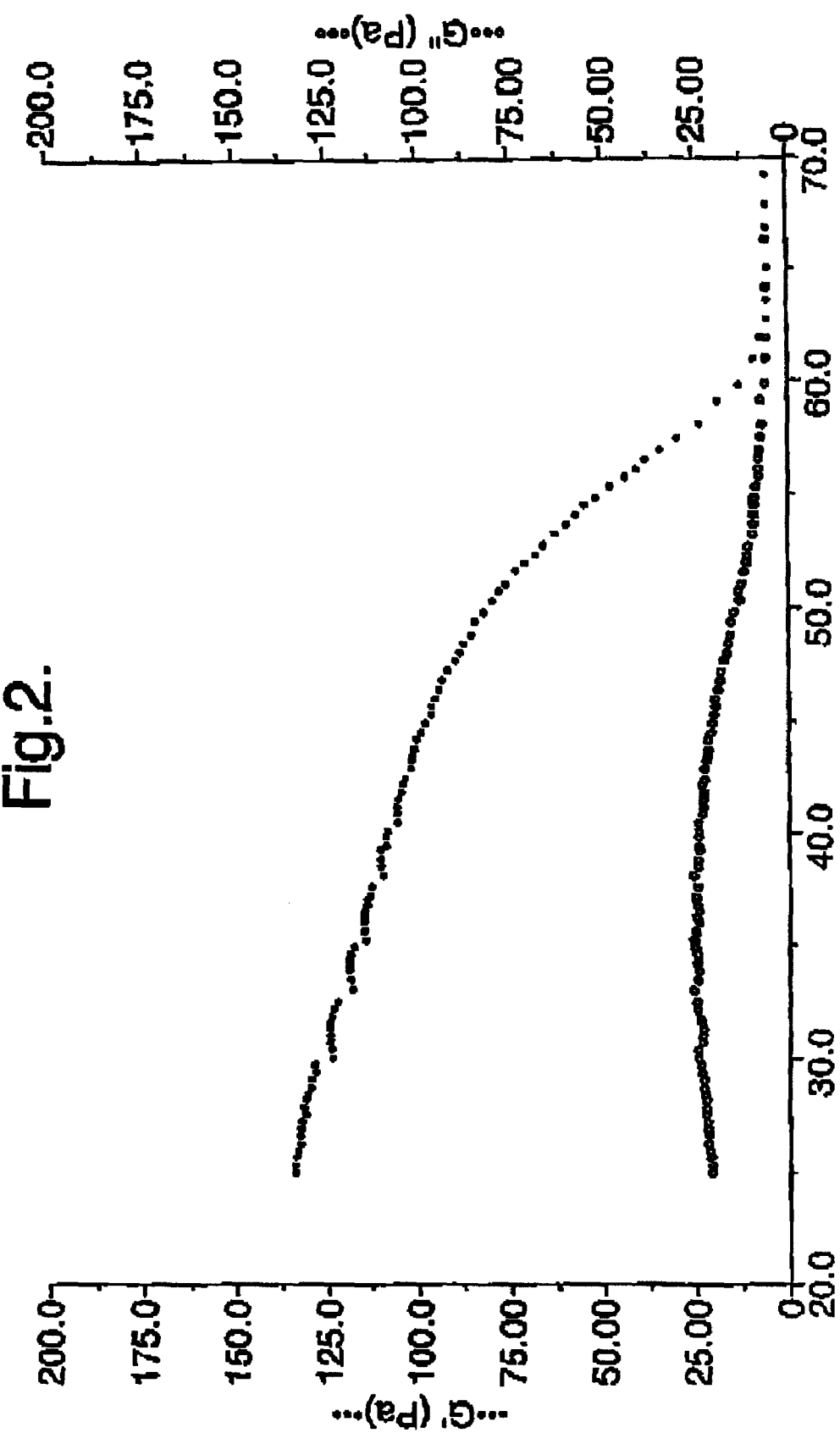
FIG. 2 shows the change in G' and G" (y axis) with temperature in ° C. (x axis) of a sheared xanthan-konjac mannan gel of 0.5% concentration in water.

Xanthan-locust bean gum controlled shear gels were prepared as follows. The individual polysaccharides were weighed and dispersed in distilled water separately. Each polysaccharide solution was heated to 90° C. while stirring with a magnetic stirrer for 1 hour. The solution was removed from the heat and water evaporation was accounted for by the addition of hot distilled water. The xanthan and locust bean gum solutions were mixed at ~90° C. in the ratios described below. The sample was transferred to the Carimed Rheometer and cooled to room temperature while shearing at a constant rate (for example $0.3s^{-1}$ or $550s^{-1}$).

Solutions were prepared at a 0.25% and 0.5% total polymer concentration and the gums were mixed at a ratio of 80:20, 50:50 and 20:80.

The variation of G' and G" as a function of frequency for 0.5% concentration xanthan-lbg gels (20:80 ratio) sheared at two different shear rates, i.e., $0.3s^{-1}$ and $550s^{-1}$ is shown in Table 1. G' was greater than G" over the frequency range studied for both samples and both are independent of frequency. G' and G" values are approximately the same for the samples sheared at $550s^{-1}$ and at $0.3s^{-1}$. The effect of controlled shear on the frequency sweeps of 0.25% concentration xanthan-lbg gels (80:20 ratio) sheared at the two different constant shear rates, i.e., $300s^{-1}$ and $550s^{-1}$ (shown in Table 2) showed that G' and G" are similar for both shear rates and that G' is greater than G" over the frequency range.

TABLE 1

| xan-lbg (0.5% conc.) in water - 550 $s^{-1}$ | | | xan-lbg (0.5% conc.) in water - 0.3 $s^{-1}$ | | |
|---|---|---|---|---|---|
| frequency (Hz) | G' (Pa) | G" (Pa) | frequency (Hz) | G' (Pa) | G" (Pa) |
| 1.00 | 31.53 | 2.21 | 1.00 | 26.10 | 1.42 |
| 1.18 | 31.79 | 2.16 | 1.18 | 26.20 | 1.47 |
| 1.39 | 32.00 | 2.20 | 1.39 | 26.46 | 1.29 |
| 1.64 | 32.03 | 2.20 | 1.64 | 26.46 | 1.51 |
| 1.93 | 32.27 | 2.31 | 1.93 | 26.25 | 1.39 |
| 2.28 | 32.45 | 2.45 | 2.28 | 26.34 | 1.38 |
| 2.68 | 33.03 | 2.78 | 2.68 | 26.26 | 1.76 |
| 3.15 | 32.51 | 2.58 | 3.15 | 26.36 | 1.54 |
| 3.72 | 31.82 | 3.04 | 3.72 | 25.73 | 1.79 |
| 4.39 | 31.44 | 2.93 | 4.39 | 25.32 | 1.99 |

TABLE 2

| xan-lbg (0.25% conc.) in water - 550 s$^{-1}$ | | | xan-lbg (0.25% conc.) in water - 300 s$^{-1}$ | | |
|---|---|---|---|---|---|
| frequency (Hz) | G' (Pa) | G" (Pa) | frequency (Hz) | G' (Pa) | G" (Pa) |
| 1.00 | 10.99 | 0.92 | 1.00 | 13.83 | 0.97 |
| 1.18 | 10.79 | 0.77 | 1.18 | 13.58 | 1.07 |
| 1.39 | 11.17 | 0.96 | 1.39 | 13.44 | 1.27 |
| 1.64 | 11.12 | 1.07 | 1.64 | 13.62 | 1.22 |
| 1.93 | 11.19 | 1.04 | 1.93 | 13.58 | 1.17 |
| 2.28 | 11.39 | 1.23 | 2.28 | 13.38 | 1.05 |
| 2.68 | 11.45 | 1.09 | 2.68 | 12.92 | 1.09 |
| 3.15 | 10.45 | 1.08 | 3.15 | 12.47 | 1.69 |

EXAMPLE 2

A non-controlled shear xanthan-locust bean gum gel was prepared as follows, Xanthan and locust bean gum powder were mixed in a weight ratio of 1:1. The mixed powder was dispersed in distilled water to form a 0.5% total polymer concentration. The solution was heated to 90° C. while stirring with a mechanical stirrer for 1 hour. The solution was removed from the heat and water evaporation was accounted for by the addition of hot distilled water. The sample was cooled to room temperature and sheared using an overhead stirrer. The mixtures were either cooled naturally with stirring to room temperature or quench cooled with stirring to about 20° C.

The variation of G' and G" with frequency at 25° C. was compared for quench cooled and naturally cooled samples. The results are shown in Table 3. For both gels G' was greater than G" over the frequency range studied for the samples and both G' and G" were independent of frequency. The results are shown in Table 3 and indicate that G' and G" are slightly higher when cooled naturally.

TABLE 3

| xan-lbg (0.5% conc.) in water - quench cooled | | | xan-lbg (0.5% conc.) in water - cooled naturally | | |
|---|---|---|---|---|---|
| frequency (Hz) | G' (Pa) | G" (Pa) | frequency (Hz) | G' (Pa) | G" (Pa) |
| 1.00 | 123.50 | 8.44 | 1.00 | 129.00 | 13.61 |
| 1.18 | 121.30 | 8.10 | 1.18 | 132.50 | 12.25 |
| 1.39 | 123.00 | 5.97 | 1.39 | 129.40 | 12.92 |
| 1.64 | 117.60 | 8.36 | 1.64 | 130.10 | 13.92 |
| 1.93 | 123.60 | 8.04 | 1.93 | 130.20 | 13.02 |
| 2.28 | 122.10 | 7.64 | 2.28 | 129.50 | 12.84 |
| 2.68 | 122.60 | 8.29 | 2.68 | 131.00 | 15.69 |
| 3.15 | 121.30 | 6.46 | 3.15 | 133.40 | 14.04 |
| 3.72 | 119.80 | 8.87 | 3.72 | 132.90 | 15.00 |
| 4.39 | 118.40 | 9.48 | 4.39 | 131.50 | 15.20 |
| 5.17 | 111.60 | 8.47 | 5.17 | 132.00 | 14.48 |
| 6.10 | 111.50 | 6.05 | 6.10 | 131.80 | 18.26 |
| 7.18 | 107.70 | 12.10 | 7.18 | 134.50 | 19.29 |
| 8.48 | 102.70 | 9.14 | 8.48 | 137.70 | 19.47 |
| 10.01 | 104.20 | 14.34 | 10.01 | 145.80 | 19.23 |

EXAMPLE 3

A xanthan-konjac mannan controlled shear gel was prepared following the procedure described in Example 1. The gums were mixed at a ratio of 1:1 and a 0.5% concentration solution was prepared. The shear rate used was 550s$^{-1}$. A non-controlled shear xanthan-konjac mannan gel was prepared using the procedure of Example 2.

G' and G" were compared for the controlled and non-controlled shear xanthan-konjac mannan gels at 25° C. The results are shown in Table 4. For both gels G' was greater than G" over the frequency range studied and both were independent of frequency. G' and G" were slightly less for the controlled shear gels than the non-controlled shear gels.

Gels were also prepared at 0.25% concentration and the effect of concentration on the frequency sweeps of xanthan-km controlled shear gels was studied. The results are shown in Table 5. For both concentrations G' was greater than G" over the whole frequency range and both were independent of frequency. G' and G" values were noticeably higher for the 0.5% concentration xanthan-km controlled shear gel than for the 0.25% concentration xanthan-km controlled gel.

TABLE 4

| xan-km (0.5% conc.) in water - controlled shear 550 1/s | | | xan-km (0.5% conc.) in water - non-controlled shear | | |
|---|---|---|---|---|---|
| frequency (Hz) | G' (Pa) | G" (Pa) | frequency (Hz) | G' (Pa) | G" (Pa) |
| 1.00 | 140.90 | 5.24 | 1.00 | 164.80 | 12.85 |
| 1.18 | 141.30 | 5.12 | 1.18 | 164.80 | 14.79 |
| 1.39 | 141.40 | 5.02 | 1.39 | 163.90 | 14.73 |
| 1.64 | 141.90 | 4.95 | 1.64 | 163.40 | 16.34 |
| 1.93 | 142.50 | 5.06 | 1.93 | 160.90 | 18.65 |
| 2.28 | 142.60 | 5.03 | 2.28 | 162.90 | 18.43 |
| 2.68 | 142.90 | 5.26 | 2.68 | 164.60 | 24.26 |
| 3.15 | 143.10 | 5.19 | 3.15 | 160.70 | 22.49 |
| 3.72 | 143.40 | 5.32 | 3.72 | 159.90 | 22.19 |
| 4.39 | 143.40 | 5.44 | 4.39 | 159.60 | 21.51 |
| 5.17 | 143.10 | 5.76 | 5.17 | 155.30 | 23.79 |
| 6.10 | 139.60 | 7.20 | 6.10 | 155.40 | 21.48 |
| 7.18 | 137.40 | 7.96 | 7.18 | 154.90 | 20.67 |
| 8.48 | 136.80 | 7.88 | 8.48 | 149.20 | 22.62 |
| 10.01 | 136.50 | 7.99 | 10.01 | 148.80 | 25.46 |

TABLE 5

| xan-km controlled shear gel at 0.25% conc. | | | xan-km controlled shear gel at 0.5% conc. | | |
|---|---|---|---|---|---|
| frequency Hz | G' Pa | G" Pa | frequency Hz | G' Pa | G" Pa |
| 1.00 | 75.86 | 3.24 | 1.00 | 140.90 | 5.24 |
| 1.18 | 75.79 | 2.92 | 1.18 | 141.30 | 5.12 |
| 1.39 | 75.86 | 3.06 | 1.39 | 141.40 | 5.02 |
| 1.64 | 75.85 | 3.04 | 1.64 | 141.90 | 4.95 |
| 1.93 | 75.64 | 3.06 | 1.93 | 142.50 | 5.06 |
| 2.28 | 75.70 | 2.95 | 2.28 | 142.60 | 5.03 |
| 2.68 | 75.46 | 2.74 | 2.68 | 142.90 | 5.26 |
| 3.15 | 75.60 | 2.93 | 3.15 | 143.10 | 5.19 |
| 3.72 | 75.03 | 3.25 | 3.72 | 143.40 | 5.32 |
| 4.39 | 73.56 | 4.49 | 4.39 | 143.40 | 5.44 |
| 5.17 | 72.80 | 3.53 | 5.17 | 143.10 | 5.76 |
| 6.10 | 72.83 | 3.69 | 6.10 | 139.60 | 7.20 |
| 7.18 | 72.07 | 3.44 | 7.18 | 137.40 | 7.96 |
| 8.48 | 72.73 | 3.78 | 8.48 | 136.80 | 7.88 |
| 10.01 | 73.21 | 4.59 | 10.01 | 136.50 | 7.99 |

EXAMPLE 4

Xanthan-lbg gels were prepared at 0.5% concentration of 1:1 xanthan: locust bean gum in water, 0.04 NaCl and 0.15 NaCl by the procedure described in Example 2.

The variation of G' and G" with frequency at 25° C. was compared for gels in water, 0.04 NaCl and 0.15 NaCl. The results are shown in Table 6. For all solutions G' was greater than G" over the whole frequency range and G' was independent of frequency for all three mixtures. The values obtained for G' and G" were higher in water and decreased in the order water>0.04M NaCl>0.15M NaCl. On cooling the onset of gelation corresponded to the sudden rise in G'. This occurred at about 57° C. for all three systems (data not shown).

TABLE 6

| xan-lbg sheared gel (0.5% conc.) in water | | | xan-lbg sheared gel (0.5% conc.) in 0.04M NaCl | | | xan-lbg sheared gel (0.5% conc.) in 0.15M NaCl | | |
|---|---|---|---|---|---|---|---|---|
| frequency Hz | G' Pa | G" Pa | frequency Hz | G' Pa | G" Pa | frequency Hz | G' Pa | G" Pa |
| 0.10 | 120.00 | 11.08 | 0.10 | 35.01 | 4.75 | 0.10 | 17.97 | 2.56 |
| 0.13 | 122.20 | 10.68 | 0.13 | 35.51 | 4.77 | 0.13 | 18.41 | 2.45 |
| 0.16 | 124.00 | 10.52 | 0.16 | 36.28 | 5.06 | 0.16 | 18.78 | 2.72 |
| 0.20 | 125.70 | 10.32 | 0.20 | 36.92 | 5.20 | 0.20 | 19.40 | 2.85 |
| 0.25 | 127.20 | 10.45 | 0.25 | 37.59 | 5.56 | 0.25 | 19.83 | 2.94 |
| 0.32 | 128.60 | 10.29 | 0.32 | 38.23 | 5.61 | 0.32 | 20.37 | 2.93 |
| 0.40 | 130.20 | 10.47 | 0.40 | 39.09 | 5.94 | 0.40 | 20.58 | 3.47 |
| 0.50 | 131.40 | 10.46 | 0.50 | 39.74 | 6.02 | 0.50 | 20.91 | 3.32 |
| 0.63 | 132.90 | 10.51 | 0.63 | 40.75 | 6.20 | 0.63 | 21.42 | 3.48 |
| 0.79 | 134.40 | 10.87 | 0.79 | 41.45 | 6.57 | 0.79 | 21.91 | 3.73 |
| 1.00 | 135.70 | 11.09 | 1.00 | 42.42 | 7.12 | 1.00 | 22.43 | 3.76 |
| 1.26 | 137.10 | 11.42 | 1.26 | 43.22 | 7.41 | 1.26 | 23.04 | 4.25 |
| 1.58 | 138.70 | 11.83 | 1.58 | 44.25 | 8.01 | 1.58 | 23.58 | 4.62 |
| 2.00 | 140.50 | 12.31 | 2.00 | 45.46 | 8.44 | 2.00 | 23.82 | 4.85 |
| 2.52 | 142.40 | 12.57 | 2.52 | 46.46 | 9.04 | 2.52 | 24.41 | 5.22 |
| 3.15 | 143.90 | 13.07 | 3.15 | 47.78 | 9.72 | 3.15 | 24.75 | 5.64 |
| 3.99 | 145.70 | 13.51 | 3.99 | 48.54 | 10.47 | 3.99 | 24.67 | 6.13 |
| 5.00 | 147.70 | 14.25 | 5.00 | 49.12 | 11.29 | 5.00 | 24.64 | 6.94 |

EXAMPLE 5

To assess the effect of alcohol. The variation of G' and G" as a function of frequency for 0.5% concentration xanthan-lbg sheared gels in water and 20% methanol was studied. The results are shown in Table 7. G' was greater than G" over the entire frequency range and neither was dependent on frequency. The values obtained for the storage and loss moduli were similar for both systems.

TABLE 7

| xan-lbg sheared gel (0.5% conc.) in water | | | xan-lbg sheared gel (0.5% conc.) in 20% methanol | | |
|---|---|---|---|---|---|
| frequency Hz | G' Pa | G" Pa | frequency Hz | G' Pa | G" Pa |
| 0.10 | 120.00 | 11.08 | 0.10 | 127.60 | 5.44 |
| 0.13 | 122.20 | 10.68 | 0.13 | 127.80 | 6.16 |
| 0.16 | 124.00 | 10.52 | 0.16 | 128.90 | 7.29 |
| 0.20 | 125.70 | 10.32 | 0.20 | 129.50 | 5.32 |
| 0.25 | 127.20 | 10.45 | 0.25 | 131.00 | 5.94 |
| 0.32 | 128.60 | 10.29 | 0.32 | 132.10 | 5.94 |
| 0.40 | 130.20 | 10.47 | 0.40 | 134.00 | 9.62 |
| 0.50 | 131.40 | 10.46 | 0.50 | 133.70 | 6.92 |
| 0.63 | 132.90 | 10.51 | 0.63 | 135.30 | 6.63 |
| 0.79 | 134.40 | 10.87 | 0.79 | 135.90 | 6.84 |
| 1.00 | 135.70 | 11.09 | 1.00 | 138.20 | 7.30 |
| 1.26 | 137.10 | 11.42 | 1.26 | 138.10 | 8.99 |
| 1.58 | 138.70 | 11.83 | 1.58 | 139.10 | 8.82 |
| 2.00 | 140.50 | 12.31 | 2.00 | 141.40 | 8.88 |
| 2.52 | 142.40 | 12.57 | 2.52 | 142.20 | 9.48 |
| 3.15 | 143.90 | 13.07 | 3.15 | 142.40 | 10.96 |
| 3.99 | 145.70 | 13.51 | 3.99 | 143.30 | 11.73 |
| 5.00 | 147.70 | 14.25 | 5.00 | 143.70 | 11.82 |
| 6.29 | 149.50 | 15.10 | 6.29 | 142.10 | 12.02 |
| 7.93 | 149.30 | 17.02 | 7.93 | 139.50 | 12.99 |
| 10.01 | 150.80 | 17.40 | 10.01 | 137.90 | 13.83 |

EXAMPLE 6

Xanthan-lbg mixtures (0.5%, 50:50) were prepared and adjusted to pH 2 and pH 10 while hot (~70° C.). The variation of G' and G" with frequency was compared for gels at pH 2, pH 5.5 and pH 10. The results are shown in Table 8. G' was greater than G" over the frequency range studied and both were independent of frequency for pH 5.5 and 10. G' and G" values were only slightly higher at pH 5.5 than in the sample adjusted to pH 10. However, for the xanthan-lbg mixture adjusted to pH 2, G" was greater than G' over the whole frequency range and both showed a strong frequency dependence (Table 8). G' and G" values at pH 2 were also lower than G' and G" values for mixtures at pH 10 or at pH 5.5.

TABLE 8

| xan-lbg sheared gel (0.5% conc.) pH 5.5 | | | xan-lbg sheared gel (0.5% conc.) @ pH 2 | | | xau-lbg sheared gel (0.5% conc.) @ pH 10 | | |
|---|---|---|---|---|---|---|---|---|
| frequency Hz | G' Pa | G" Pa | frequency Hz | G' Pa | G" Pa | frequency Hz | G' Pa | G" Pa |
| 0.10 | 120.00 | 11.08 | 0.10 | 0.05 | 0.24 | 0.10 | 90.67 | 8.03 |
| 0.13 | 122.20 | 10.68 | 0.13 | 0.07 | 0.30 | 0.13 | 92.68 | 7.39 |
| 0.16 | 124.00 | 10.52 | 0.16 | 0.10 | 0.36 | 0.16 | 95.38 | 7.21 |
| 0.20 | 125.70 | 10.32 | 0.20 | 0.15 | 0.43 | 0.20 | 95.66 | 8.02 |
| 0.25 | 127.20 | 10.45 | 0.25 | 0.20 | 0.51 | 0.25 | 97.07 | 7.26 |
| 0.32 | 128.60 | 10.29 | 0.32 | 0.25 | 0.60 | 0.32 | 98.53 | 7.02 |
| 0.40 | 130.20 | 10.47 | 0.40 | 0.33 | 0.70 | 0.40 | 98.99 | 7.29 |
| 0.50 | 131.40 | 10.46 | 0.50 | 0.40 | 0.81 | 0.50 | 99.80 | 7.43 |
| 0.63 | 132.90 | 10.51 | 0.63 | 0.49 | 0.93 | 0.63 | 101.70 | 7.45 |
| 0.79 | 134.40 | 10.87 | 0.79 | 0.62 | 1.08 | 0.79 | 102.50 | 8.10 |
| 1.00 | 135.70 | 11.09 | 1.00 | 0.69 | 1.24 | 1.00 | 104.30 | 7.91 |
| 1.26 | 137.10 | 11.42 | 1.26 | 0.83 | 1.37 | 1.26 | 105.70 | 8.08 |
| 1.58 | 138.70 | 11.83 | 1.58 | 0.91 | 1.55 | 1.58 | 105.80 | 8.57 |
| 2.00 | 140.50 | 12.31 | 2.00 | 1.05 | 1.90 | 2.00 | 107.00 | 8.26 |
| 2.52 | 142.40 | 12.57 | 2.52 | 0.93 | 2.08 | 2.52 | 108.70 | 8.49 |
| 3.15 | 143.90 | 13.07 | | | | 3.15 | 109.50 | 9.26 |
| 3.99 | 145.70 | 13.51 | | | | 3.99 | 109.70 | 9.06 |
| 5.00 | 147.70 | 14.25 | | | | 5.00 | 110.90 | 9.84 |
| 6.29 | 149.50 | 15.10 | | | | 6.29 | 111.40 | 10.67 |
| 7.93 | 149.30 | 17.02 | | | | 7.93 | 110.60 | 11.20 |
| 10.01 | 150.80 | 17.40 | | | | 10.01 | 110.60 | 11.19 |

EXAMPLE 7

Xanthan-lbg mixtures (0.5%, 50:50) were prepared by heating the aqueous polysaccharide solutions to 90° C., 70° C. and 50° C. using the procedure outlined in example 2. The mixed solutions were then cooled naturally and sheared.

The variation of G' and G" with frequency for gels mixed at 90° C., 70° C. and 50° C. was compared. The results are shown in Table 9. For all three samples G' was greater than G" at 25° C. over the entire frequency range and all were independent of frequency. From the three temperatures studied, it is seen that G' and G" increase when the mixture is subjected to higher temperatures.

TABLE 9

| xan-lbg sheared gel (0.5% conc.) in water 90° C. | | | xan-lbg sheared gel (0.5% conc.) in water 70° C. | | | xan-lbg sheared gel (0.5% conc.) in water 50° C. | | |
|---|---|---|---|---|---|---|---|---|
| frequency Hz | G' Pa | G" Pa | frequency Hz | G' Pa | G" Pa | frequency Hz | G' Pa | G" Pa |
| 0.10 | 120.00 | 11.08 | 0.10 | 86.52 | 9.96 | 0.10 | 75.02 | 6.38 |
| 0.13 | 122.20 | 10.68 | 0.13 | 88.49 | 9.53 | 0.13 | 75.66 | 5.57 |
| 0.16 | 124.00 | 10.52 | 0.16 | 90.33 | 9.12 | 0.16 | 76.05 | 5.77 |
| 0.20 | 125.70 | 10.32 | 0.20 | 91.86 | 9.02 | 0.20 | 76.47 | 5.26 |
| 0.25 | 127.20 | 10.45 | 0.25 | 92.93 | 8.91 | 0.25 | 76.83 | 5.32 |
| 0.32 | 128.60 | 10.29 | 0.32 | 94.40 | 9.31 | 0.32 | 77.49 | 5.70 |
| 0.40 | 130.20 | 10.47 | 0.40 | 95.33 | 9.07 | 0.40 | 78.41 | 4.95 |
| 0.50 | 131.40 | 10.46 | 0.50 | 96.47 | 9.33 | 0.50 | 78.86 | 5.43 |
| 0.63 | 132.90 | 10.51 | 0.63 | 97.55 | 9.31 | 0.63 | 79.16 | 5.08 |
| 0.79 | 134.40 | 10.87 | 0.79 | 98.76 | 9.98 | 0.79 | 79.68 | 5.14 |
| 1.00 | 135.70 | 11.09 | 1.00 | 99.97 | 10.22 | 1.00 | 80.48 | 5.39 |
| 1.26 | 137.10 | 11.42 | 1.26 | 101.20 | 10.50 | 1.26 | 80.70 | 4.97 |
| 1.58 | 138.70 | 11.83 | 1.58 | 102.60 | 10.94 | 1.58 | 81.32 | 5.37 |
| 2.00 | 140.50 | 12.31 | 2.00 | 103.90 | 11.32 | 2.00 | 81.65 | 5.60 |
| 2.52 | 142.40 | 12.57 | 2.52 | 105.50 | 11.71 | 2.52 | 82.33 | 5.54 |
| 3.15 | 143.90 | 13.07 | 3.15 | 107.20 | 12.05 | 3.15 | 82.93 | 6.13 |
| 3.99 | 145.70 | 13.51 | 3.99 | 108.90 | 12.81 | 3.99 | 83.26 | 6.27 |
| 5.00 | 147.70 | 14.25 | 5.00 | 109.70 | 13.64 | 5.00 | 83.57 | 6.70 |
| 6.29 | 149.50 | 15.10 | 6.29 | 110.80 | 15.38 | 6.29 | 83.36 | 6.53 |
| 7.93 | 149.30 | 17.02 | 7.93 | 111.50 | 15.44 | 7.93 | 83.15 | 7.17 |
| 10.01 | 150.80 | 17.40 | 10.01 | 113.10 | 15.86 | 10.01 | 83.62 | 7.72 |

EXAMPLE 8

Xanthan-konjac mannan gels were prepared at a ratio of 1:1 and stirred at 550 rpm to study the effect of the rate of cooling.

The variation of G' and G" with frequency for xanthan-konjac mannan gels was compared for naturally cooled and quench cooled gels. The results are shown in Table 10. For both the quench cooled and naturally cooled samples G' was greater than G" over the frequency range studied and both were independent of frequency. However, G' and G" values obtained for the xanthan-km mixture cooled naturally to room temperature were higher than those obtained for the quench cooled mixture.

TABLE 10

| xan-km sheared gel (0.5% conc.) in water cooled naturally | | | xan-km sheared gel (0.5% conc.) in water quench cooled | | |
|---|---|---|---|---|---|
| frequency Hz | G' Pa | G" Pa | frequency Hz | G' Pa | G" Pa |
| 1.00 | 164.80 | 12.85 | 1.00 | 78.11 | 6.41 |
| 1.18 | 164.80 | 14.79 | 1.18 | 83.05 | 7.80 |
| 1.39 | 163.90 | 14.73 | 1.39 | 81.28 | 5.31 |
| 1.64 | 163.40 | 16.34 | 1.64 | 78.16 | 7.70 |
| 1.93 | 160.90 | 18.65 | 1.93 | 79.16 | 7.54 |
| 2.28 | 162.90 | 18.43 | 2.28 | 81.60 | 5.88 |
| 2.68 | 164.60 | 24.26 | 2.68 | 80.80 | 6.28 |
| 3.15 | 160.70 | 22.49 | 3.15 | 79.48 | 8.18 |
| 3.72 | 159.90 | 22.19 | 3.72 | 74.65 | 6.55 |
| 4.39 | 159.60 | 21.51 | 4.39 | 73.99 | 6.98 |
| 5.17 | 155.30 | 23.79 | 5.17 | 73.89 | 8.76 |
| 6.10 | 155.40 | 21.48 | 6.10 | 70.37 | 6.70 |
| 7.18 | 154.90 | 20.67 | 7.18 | 66.47 | 6.03 |
| 8.48 | 149.20 | 22.62 | 8.48 | 66.28 | 8.74 |
| 10.01 | 148.80 | 25.46 | 10.01 | 64.07 | 9.00 |

EXAMPLE 9

Xanthan-km sheared gels were prepared at 0.5% concentration in water, 0.04M NaCl and 0.15M NaCl. The variation of G' and G" with frequency was compared for the three samples. The results are shown in Table 11. Typical gel-like spectra (i.e. G' is always higher than G" and independent of frequency) were obtained for all three samples. G' and G" values are appreciably higher in the absence of electrolyte and decrease in the order no electrolyte>0.04M NaCl>0.15M NaCl.

The effect of zinc chloride on xanthan-km systems was also studied. The results are shown in Table 12. The variation of G' and G" as a function of frequency for xanthan-km sheared gels in water and 0.1M $ZnCl_2$ were compared. G' and G" values were significantly higher in water than in zinc chloride.

TABLE 11

| xan-km sheared gel (0.5% conc.) in water | | | xan-km sheared gel (0.5% conc.) in 0.04 M NaCl | | | xan-km sheared gel (0.5% conc.) in 0.15 M NaCl | | |
|---|---|---|---|---|---|---|---|---|
| frequency Hz | G' Pa | G" Pa | frequency Hz | G' Pa | G" Pa | frequency Hz | G' Pa | G" Pa |
| 1.00 | 145.80 | 21.58 | 1.00 | 52.23 | 6.36 | 1.00 | 26.53 | 8.95 |
| 1.26 | 148.20 | 21.27 | 1.26 | 52.89 | 6.85 | 1.18 | 27.44 | 9.32 |
| 1.58 | 150.70 | 21.04 | 1.58 | 53.99 | 7.24 | 1.39 | 28.39 | 9.67 |
| 2.00 | 153.20 | 21.43 | 2.00 | 55.08 | 7.67 | 1.64 | 29.34 | 9.96 |
| 2.52 | 156.20 | 21.41 | 2.52 | 56.21 | 8.14 | 1.93 | 30.26 | 10.37 |
| 3.15 | 159.00 | 20.46 | 3.15 | 57.03 | 8.62 | 2.28 | 31.38 | 10.65 |
| 3.99 | 161.40 | 20.73 | 3.99 | 57.57 | 9.40 | 2.68 | 32.76 | 11.19 |
| 5.00 | 164.60 | 20.68 | 5.00 | 57.20 | 9.83 | 3.15 | 33.55 | 11.61 |
| 6.29 | 166.90 | 20.71 | 6.29 | 57.54 | 11.00 | 3.72 | 34.71 | 12.12 |
| 7.93 | 167.40 | 21.74 | 7.93 | 57.14 | 11.54 | 4.39 | 35.55 | 12.40 |
| 10.01 | 168.90 | 20.73 | 10.01 | 57.54 | 12.74 | 5.17 | 36.52 | 12.75 |
| | | | | | | 6.10 | 37.58 | 12.99 |
| | | | | | | 7.18 | 38.51 | 13.30 |
| | | | | | | 8.48 | 39.57 | 13.91 |
| | | | | | | 10.01 | 41.31 | 14.38 |

TABLE 12

| xan-km sheared gel (0.5% conc.) in water | | | xan-km sheared gel (0.5% conc.) in 0.1 M $ZnCl_2$ | | |
|---|---|---|---|---|---|
| frequency Hz | G' Pa | G" Pa | frequency Hz | G' Pa | G" Pa |
| 0.10 | 127.20 | 20.90 | 1.00 | 35.67 | 12.87 |
| 0.13 | 129.40 | 20.66 | 1.18 | 37.46 | 13.17 |
| 0.16 | 130.30 | 22.11 | 1.39 | 39.21 | 13.52 |
| 0.20 | 132.50 | 21.05 | 1.64 | 40.75 | 13.78 |
| 0.25 | 133.60 | 21.24 | 1.93 | 42.34 | 14.17 |
| 0.32 | 135.10 | 21.27 | 2.28 | 44.10 | 14.73 |
| 0.40 | 137.10 | 21.88 | 2.68 | 46.19 | 15.11 |
| 0.50 | 138.50 | 21.90 | 3.15 | 47.86 | 15.55 |
| 0.63 | 141.10 | 21.83 | 3.72 | 49.10 | 16.08 |
| 0.79 | 143.40 | 21.36 | 4.39 | 50.69 | 16.47 |
| 1.00 | 145.80 | 21.58 | 5.17 | 51.80 | 16.73 |
| 1.26 | 148.20 | 21.27 | 6.10 | 52.82 | 17.04 |
| 1.58 | 150.70 | 21.04 | 7.18 | 53.88 | 17.01 |
| 2.00 | 153.20 | 21.43 | 8.48 | 54.98 | 17.46 |
| 2.52 | 156.20 | 21.41 | 10.01 | 55.93 | 17.91 |
| 3.15 | 159.00 | 20.46 | | | |
| 3.99 | 161.40 | 20.73 | | | |
| 5.00 | 164.60 | 20.68 | | | |
| 6.29 | 166.90 | 20.71 | | | |
| 7.93 | 167.40 | 21.74 | | | |
| 10.01 | 168.90 | 20.73 | | | |

EXAMPLE 10

20% methanol at 70° C. was added to a xanthan-km mixture at 70° C. with stirring and was cooled (with and without stirring) to room temperature. The variation of G' and G" with frequency was compared for sheared and non-sheared gels in 20% methanol. The results are shown in Table 13. G' is greater than G" over the full frequency range for both the sheared and non-sheared gels and both are independent of frequency. G' values are higher for the xanthan-km non-sheared gels in 20% methanol than for the sheared gel. G' values obtained for the sheared gel containing 20% methanol are slightly greater than those obtained for the xanthan-km sheared gel in water. These results are shown in Table 14.

The variation of G' and G" as a function of temperature for a xanthan-km sheared gel on heating and cooling was also studied. The results are shown in Table 15. G' values become higher on cooling from 65–35° C. The sheared gel melts at ~62° C. on heating and the onset of gelation on cooling also occurs at ~62° C. These values are similar to the values of melting and gelation obtained in water.

TABLE 13

| xan-km sheared gel (0.5% conc.) in 20% methanol | | | xan-km non-sheared gel (0.5% conc.) in 20% methanol | | |
|---|---|---|---|---|---|
| frequency Hz | G' Pa | G" Pa | frequency Hz | G' Pa | G" Pa |
| 0.10 | 158.40 | 2.54 | 0.10 | 183.50 | 10.70 |
| 0.13 | 159.90 | 5.93 | 0.13 | 188.60 | 6.54 |
| 0.16 | 160.50 | 3.25 | 0.16 | 189.00 | 8.49 |
| 0.20 | 160.40 | 3.28 | 0.20 | 190.70 | 6.76 |
| 0.25 | 162.30 | 6.02 | 0.25 | 190.30 | 7.52 |
| 0.32 | 162.60 | 5.70 | 0.32 | 193.60 | 6.84 |
| 0.40 | 163.30 | 3.57 | 0.40 | 194.80 | 2.80 |
| 0.50 | 164.20 | 4.37 | 0.50 | 194.50 | 4.26 |
| 0.63 | 163.70 | 5.66 | 0.63 | 196.60 | 4.01 |
| 0.79 | 164.20 | 4.42 | 0.79 | 194.40 | 3.22 |
| 1.00 | 167.10 | 4.81 | 1.00 | 196.90 | 5.99 |
| 1.26 | 166.30 | 3.49 | 1.26 | 196.20 | 5.25 |
| 1.58 | 167.50 | 5.97 | 1.58 | 195.80 | 3.54 |
| 2.00 | 169.80 | 6.20 | 2.00 | 197.30 | 4.36 |
| 2.52 | 168.00 | 7.13 | 2.52 | 197.80 | 5.14 |
| 3.15 | 170.50 | 7.01 | 3.15 | 197.40 | 3.44 |
| 3.99 | 172.00 | 7.81 | 3.99 | 197.60 | 5.33 |
| 5.00 | 171.80 | 8.78 | 5.00 | 198.90 | 5.35 |
| 6.29 | 173.30 | 8.42 | 6.29 | 196.90 | 7.27 |
| 7.93 | 172.30 | 9.58 | 7.93 | 190.00 | 13.16 |
| 10.01 | 170.60 | 10.16 | 10.01 | 184.80 | 15.58 |

TABLE 14

| xan-km sheared gel (0.5% conc.) in water | | | xan-km sheared gel (0.5% conc.) in 20% methanol | | |
|---|---|---|---|---|---|
| frequency Hz | G' Pa | G" Pa | frequency Hz | G' Pa | G" Pa |
| 0.10 | 127.20 | 20.90 | 0.10 | 158.40 | 2.54 |
| 0.13 | 129.40 | 20.66 | 0.13 | 159.90 | 5.93 |
| 0.16 | 130.30 | 22.11 | 0.16 | 160.50 | 3.25 |
| 0.20 | 132.50 | 21.05 | 0.20 | 160.40 | 3.28 |
| 0.25 | 133.60 | 21.24 | 0.25 | 162.30 | 6.02 |
| 0.32 | 135.10 | 21.27 | 0.32 | 162.60 | 5.70 |
| 0.40 | 137.10 | 21.88 | 0.40 | 163.30 | 3.57 |
| 0.50 | 138.50 | 21.90 | 0.50 | 164.20 | 4.37 |
| 0.63 | 141.10 | 21.83 | 0.63 | 163.70 | 5.66 |
| 0.79 | 143.40 | 21.36 | 0.79 | 164.20 | 4.42 |
| 1.00 | 145.80 | 21.58 | 1.00 | 167.10 | 4.81 |
| 1.26 | 148.20 | 21.27 | 1.26 | 166.30 | 3.49 |
| 1.58 | 150.70 | 21.04 | 1.58 | 167.50 | 5.97 |
| 2.00 | 153.20 | 21.43 | 2.00 | 169.80 | 6.20 |
| 2.52 | 156.20 | 21.41 | 2.52 | 168.00 | 7.13 |
| 3.15 | 159.00 | 20.46 | 3.15 | 170.50 | 7.01 |
| 3.99 | 161.40 | 20.73 | 3.99 | 172.00 | 7.81 |
| 5.00 | 164.60 | 20.68 | 5.00 | 171.80 | 8.78 |
| 6.29 | 166.90 | 20.71 | 6.29 | 173.30 | 8.42 |
| 7.93 | 167.40 | 21.74 | 7.93 | 172.30 | 9.58 |
| 10.01 | 168.90 | 20.73 | 10.01 | 170.60 | 10.16 |

TABLE 15 xan-km (0.5% conc.) in 20% methanol heating cycle

| temp. Deg C. | G' Pa | G" Pa | temp. Deg C. | G' Pa | G" Pa | temp. Deg C. | G' Pa | G" Pa |
|---|---|---|---|---|---|---|---|---|
| 35.00 | 152.30 | 6.79 | 47.70 | 104.40 | 11.09 | 52.70 | 82.63 | 7.49 |
| 35.30 | 146.40 | 8.22 | 48.00 | 105.80 | 6.90 | 52.90 | 80.60 | 6.86 |
| 35.70 | 148.10 | 7.82 | 48.30 | 103.60 | 6.60 | 53.30 | 77.23 | 6.01 |
| 36.00 | 146.40 | 8.26 | 48.60 | 102.20 | 8.62 | 53.60 | 74.57 | 6.13 |
| 36.30 | 146.60 | 8.10 | 48.90 | 99.69 | 10.82 | 61.70 | 10.05 | 4.87 |
| 36.60 | 144.80 | 9.38 | 49.20 | 100.90 | 7.99 | 62.00 | 8.55 | 4.72 |
| 36.80 | 139.70 | 12.88 | 49.60 | 99.55 | 8.35 | 62.40 | 7.36 | 4.46 |
| 37.10 | 140.30 | 8.39 | 49.90 | 97.87 | 9.18 | 62.60 | 6.24 | 4.20 |
| 37.40 | 139.80 | 8.38 | 50.20 | 97.44 | 7.45 | 63.00 | 5.22 | 3.94 |
| 37.80 | 138.80 | 8.85 | 50.50 | 94.80 | 9.24 | 63.30 | 4.38 | 3.72 |
| 38.20 | 136.20 | 6.66 | 50.80 | 93.17 | 6.38 | 63.60 | 3.78 | 3.59 |
| 38.40 | 136.60 | 7.12 | 51.10 | 91.73 | 7.06 | 64.00 | 3.35 | 3.48 |
| 38.80 | 135.40 | 8.41 | 51.40 | 90.05 | 7.10 | 64.20 | 3.15 | 3.41 |
| 39.00 | 133.70 | 8.26 | 51.70 | 88.96 | 7.80 | 64.60 | 3.12 | 3.40 |
| 47.10 | 108.00 | 8.93 | 52.00 | 87.85 | 6.74 | 64.90 | 3.06 | 3.34 |
| 47.40 | 108.00 | 7.45 | 52.30 | 85.13 | 6.84 | 65.20 | 2.97 | 3.34 |

TABLE 15-continued

| temp. Deg C. | G' Pa | G" Pa | temp. Deg C. | G' Pa | G" Pa | temp. Deg C. | G' Pa | G" Pa |
|---|---|---|---|---|---|---|---|---|
| xan-km (0.5% conc.) in 20% methanol cooling cycle ||||||||||
| 65.20 | 3.44 | 3.86 | 54.70 | 44.01 | 2.99 | 44.60 | 136.70 | 5.31 |
| 64.80 | 3.49 | 3.86 | 54.40 | 45.90 | 3.08 | 44.40 | 139.80 | 4.10 |
| 64.50 | 3.48 | 3.90 | 54.10 | 48.99 | 2.94 | 44.00 | 143.10 | 5.72 |
| 64.20 | 3.50 | 3.91 | 53.80 | 52.35 | 2.48 | 43.70 | 147.30 | 5.47 |
| 63.90 | 3.54 | 3.92 | 53.50 | 55.36 | 2.04 | 43.40 | 151.60 | 4.78 |
| 63.60 | 3.63 | 3.93 | 53.10 | 57.11 | 2.78 | 43.10 | 151.00 | 5.23 |
| 63.30 | 3.66 | 3.98 | 52.80 | 60.35 | 2.36 | 42.70 | 154.40 | 4.95 |
| 62.90 | 3.76 | 4.03 | 52.50 | 63.38 | 2.56 | 42.40 | 154.10 | 3.39 |
| 62.70 | 3.85 | 3.96 | 52.20 | 64.06 | 2.60 | 42.10 | 156.70 | 7.77 |
| 62.30 | 3.97 | 4.01 | 51.90 | 67.19 | 2.27 | 41.80 | 159.20 | 8.45 |
| 62.00 | 4.20 | 4.07 | 51.60 | 71.64 | 2.44 | 41.50 | 160.60 | 6.26 |
| 61.40 | 4.94 | 4.16 | 51.20 | 73.43 | 3.12 | 41.10 | 164.10 | 6.25 |
| 61.10 | 5.64 | 4.28 | 50.90 | 77.70 | 3.37 | 40.80 | 167.80 | 6.08 |
| 60.80 | 6.38 | 4.29 | 50.60 | 79.84 | 2.38 | 40.50 | 169.30 | 6.90 |
| 60.40 | 7.36 | 4.31 | 50.30 | 82.58 | 3.33 | 40.20 | 166.10 | 5.75 |
| 60.10 | 8.36 | 4.27 | 50.00 | 86.04 | 2.74 | 39.90 | 173.80 | 6.48 |
| 59.80 | 9.53 | 4.34 | 49.70 | 87.92 | 3.61 | 39.60 | 174.00 | 6.04 |
| 59.50 | 11.02 | 4.30 | 49.30 | 91.23 | 2.74 | 39.30 | 175.10 | 12.64 |
| 59.20 | 12.69 | 4.09 | 49.00 | 94.40 | 3.72 | 38.90 | 180.80 | 10.23 |
| 58.90 | 14.45 | 4.04 | 48.80 | 97.57 | 3.38 | 38.70 | 185.40 | 7.21 |
| 58.50 | 16.23 | 4.02 | 48.40 | 101.30 | 3.56 | 38.40 | 187.70 | 6.17 |
| 58.20 | 17.92 | 3.87 | 48.10 | 104.90 | 6.20 | 38.00 | 189.50 | 7.42 |
| 57.90 | 20.00 | 3.93 | 47.80 | 110.60 | 5.09 | 37.70 | 184.00 | 5.73 |
| 57.60 | 22.00 | 3.64 | 47.50 | 111.30 | 4.38 | 37.40 | 192.10 | 7.09 |
| 57.30 | 24.52 | 3.53 | 47.20 | 116.40 | 3.70 | 37.10 | 195.50 | 6.52 |
| 57.00 | 26.47 | 3.39 | 46.80 | 119.50 | 3.65 | 36.80 | 197.70 | 7.22 |
| 56.70 | 28.93 | 3.03 | 46.50 | 123.20 | 4.28 | 36.50 | 197.90 | 7.91 |
| 56.30 | 31.11 | 3.37 | 46.20 | 126.50 | 5.46 | 36.30 | 199.40 | 6.73 |
| 56.00 | 33.56 | 3.02 | 45.90 | 128.90 | 3.78 | 35.90 | 198.80 | 7.92 |
| 55.70 | 36.09 | 2.75 | 45.60 | 134.10 | 5.00 | 35.60 | 200.80 | 7.24 |
| 55.40 | 38.77 | 2.96 | 45.30 | 133.70 | 5.92 | 35.30 | 191.10 | 8.51 |
| 55.10 | 41.54 | 2.61 | 44.90 | 132.40 | 4.04 | 35.00 | 201.90 | 5.75 |

EXAMPLE 11

Xanthan-km mixtures (0.5% 50:50) were prepared and adjusted to pH 2 and pH 10 while at ~70° C. The variation of G' and G" as a function of frequency for xanthan-km sheared gels at pH 5.5, at pH 2 and pH 10 was compared. The results are shown in Table 16. For xanthan-km sheared gels at pH 5.5 and at pH 10, G' is higher than G" at all frequency levels and neither are dependent on frequency. The G' values for the sheared gels at pH 5.5 and at pH 10 are very similar. However, for the xanthan-km stirred gel adjusted to pH 2, both moduli are frequency dependent and G" is slightly greater than G' over the frequency range 0.1–0.3 Hz where they cross over and G' becomes greater than G". This behaviour is typical of an entangled network and no gel-like characteristics are apparent.

TABLE 16

| xan-km sheared gel (0.5% conc.) @ pH 5.5 ||| xan-km sheared gel (0.5% conc.) @ pH 2 ||| xan-km sheared gel (0.5% conc.) @ pH 10 |||
|---|---|---|---|---|---|---|---|---|
| frequency Hz | G' Pa | G" Pa | frequency Hz | G' Pa | G" Pa | frequency Hz | G' Pa | G" Pa |
| 0.10 | 127.20 | 20.90 | 0.10 | 2.16 | 2.51 | 0.10 | 123.60 | 4.73 |
| 0.13 | 129.40 | 20.66 | 0.13 | 2.49 | 2.81 | 0.13 | 122.60 | 4.24 |
| 0.16 | 130.30 | 22.11 | 0.16 | 2.87 | 3.12 | 0.16 | 125.10 | 4.64 |
| 0.20 | 132.50 | 21.05 | 0.20 | 3.25 | 3.44 | 0.20 | 125.00 | 4.32 |
| 0.25 | 133.60 | 21.24 | 0.25 | 3.79 | 3.82 | 0.25 | 125.80 | 5.07 |
| 0.32 | 135.10 | 21.27 | 0.32 | 4.32 | 4.21 | 0.32 | 127.20 | 2.35 |
| 0.40 | 137.10 | 21.88 | 0.40 | 4.94 | 4.57 | 0.40 | 126.90 | 5.35 |
| 0.50 | 138.50 | 21.90 | 0.50 | 5.53 | 5.00 | 0.50 | 127.50 | 5.04 |
| 0.63 | 141.10 | 21.83 | 0.63 | 6.23 | 5.44 | 0.63 | 128.50 | 5.23 |
| 0.79 | 143.40 | 21.36 | 0.79 | 6.99 | 5.87 | 0.79 | 130.00 | 3.05 |
| 1.00 | 145.80 | 21.58 | 1.00 | 7.87 | 6.30 | 1.00 | 129.20 | 5.86 |
| 1.26 | 148.20 | 21.27 | 1.26 | 8.77 | 6.81 | 1.26 | 131.20 | 5.44 |
| 1.58 | 150.70 | 21.04 | 1.58 | 9.65 | 7.34 | 1.58 | 131.20 | 5.20 |
| 2.00 | 153.20 | 21.43 | 2.00 | 10.59 | 7.76 | 2.00 | 132.50 | 5.01 |
| 2.52 | 156.20 | 21.41 | 2.52 | 11.54 | 8.30 | 2.52 | 133.20 | 6.69 |
| 3.15 | 159.00 | 20.46 | 3.15 | 12.41 | 8.72 | 3.15 | 135.00 | 6.69 |
| 3.99 | 161.40 | 20.73 | 3.99 | 13.13 | 9.32 | 3.99 | 136.40 | 6.86 |
| 5.00 | 164.60 | 20.68 | 5.00 | 13.51 | 9.79 | 5.00 | 137.90 | 8.20 |
| 6.29 | 166.90 | 20.71 | | | | 6.29 | 139.30 | 8.32 |

TABLE 16-continued

| xan-km sheared gel (0.5% conc.) @ pH 5.5 | | | xan-km sheared gel (0.5% conc.) @ pH 2 | | | xan-km sheared gel (0.5% conc.) @ pH 10 | | |
|---|---|---|---|---|---|---|---|---|
| frequency Hz | G' Pa | G" Pa | frequency Hz | G' Pa | G" Pa | frequency Hz | G' Pa | G" Pa |
| 7.93 | 167.40 | 21.74 | | | | 7.93 | 136.90 | 9.60 |
| 10.01 | 168.90 | 20.73 | | | | 10.01 | 141.10 | 9.42 |

EXAMPLE 12

Xanthan-km mixtures, (0.5% 50:50) were prepared by heating the polysaccharides to 90° C., 70° C. and 50° C. in water and electrolyte using the procedure outlined in Example 7. The variation of G' and G" for xanthan-km sheared gels at 25° C. in water for the three mixing temperatures was studied as a function of frequency. The results are shown in Table 17. For all three samples G' is greater than G" over the whole frequency range. Samples heated to 90° C. and 70° C. were independent of frequency and had almost identical G' and G" values. However, a slight frequency dependence of the storage modulus over the entire frequency range was observed for the xanthan-km mixtures heated to 50° C. indicating perhaps that the lower the temperature the xanthan-km mixtures are heated to, the lower the value of G' and the more frequency dependent it becomes therefore resulting in a decrease in gel strength.

The variations of G' and G" as a function of frequency for xanthan-km sheared gels at 25° C. which were heated to 90° C., 70° C. and 50° C. in 0.15M NaCl were measured. The results are shown in Table 18. The gels show a typical gel-like response at all frequency levels studied. G' is always higher than G" but all three samples are slightly frequency dependent. The magnitude of G' is significantly less in 0.15M NaCl compared to water for samples prepared at 90° C. and 70° C. At 50° C. there is no noticeable reduction in G'.

The effect of mixing temperature on xanthan-km gels in 0.1M $ZnCl_2$ was also studied. G' and G" were measured as a function of frequency for xanthan-km sheared gels at 25° C. which were heated to 90° C., 70° C. and 50° C. in 0.1M $ZnCl_2$. The results are shown in Table 19. For all three samples G' is greater than G" over the frequency range studied but all three show a slight frequency dependence. G' and G" values are only slightly higher for the sample heated to 90° C. in comparison to those heated to 70° C. and 50° C.

TABLE 17

| xan-km sheared gel (0.5% conc.) in water heated to 90° C. | | | xan-km sheared gel (0.5% conc.) in water heated to 70° C. | | | xan-km sheared gel (0.5% conc.) in water heated to 50° C. | | |
|---|---|---|---|---|---|---|---|---|
| frequency Hz | G' Pa | G" Pa | frequency Hz | G' Pa | G" Pa | frequency Hz | G' Pa | G" Pa |
| 0.10 | 127.20 | 20.90 | 0.10 | 133.60 | 14.52 | 0.10 | 39.88 | 11.94 |
| 0.13 | 129.40 | 20.66 | 0.13 | 135.70 | 15.19 | 0.13 | 42.16 | 11.97 |
| 0.16 | 130.30 | 22.11 | 0.16 | 136.60 | 15.50 | 0.16 | 43.93 | 11.96 |
| 0.20 | 132.50 | 21.05 | 0.20 | 137.80 | 15.42 | 0.20 | 45.53 | 11.84 |
| 0.25 | 133.60 | 21.24 | 0.25 | 138.00 | 16.12 | 0.25 | 47.49 | 11.92 |
| 0.32 | 135.10 | 21.27 | 0.32 | 139.70 | 16.12 | 0.32 | 48.60 | 12.25 |
| 0.40 | 137.10 | 21.88 | 0.40 | 140.00 | 16.34 | 0.40 | 50.09 | 11.99 |
| 0.50 | 138.50 | 21.90 | 0.50 | 141.40 | 16.15 | 0.50 | 52.01 | 11.97 |
| 0.63 | 141.10 | 21.83 | 0.63 | 142.70 | 16.51 | 0.63 | 53.47 | 12.02 |
| 0.79 | 143.40 | 21.36 | 0.79 | 144.00 | 16.87 | 0.79 | 54.67 | 12.41 |
| 1.00 | 145.80 | 21.58 | 1.00 | 145.50 | 17.15 | 1.00 | 56.24 | 12.54 |
| 1.26 | 148.20 | 21.27 | 1.26 | 147.40 | 17.78 | 1.26 | 58.08 | 12.72 |
| 1.58 | 150.70 | 21.04 | 1.58 | 149.50 | 18.18 | 1.58 | 59.94 | 13.14 |
| 2.00 | 153.20 | 21.43 | 2.00 | 151.70 | 18.73 | 2.00 | 61.73 | 13.18 |
| 2.52 | 156.20 | 21.41 | 2.52 | 154.20 | 19.41 | 2.52 | 63.83 | 13.79 |
| 3.15 | 159.00 | 20.46 | 3.15 | 156.60 | 19.41 | 3.15 | 65.39 | 13.97 |
| 3.99 | 161.40 | 20.73 | 3.99 | 159.10 | 20.36 | 3.99 | 67.16 | 14.44 |
| 5.00 | 164.60 | 20.68 | 5.00 | 161.90 | 21.28 | 5.00 | 68.50 | 15.18 |
| 6.29 | 166.90 | 20.71 | 6.29 | 164.20 | 21.69 | 6.29 | 69.99 | 15.20 |
| 7.93 | 167.40 | 21.74 | 7.93 | 165.40 | 24.51 | 7.93 | 71.43 | 15.75 |
| 10.01 | 168.90 | 20.73 | 10.01 | 166.70 | 22.71 | 10.01 | 74.41 | 16.20 |

TABLE 18

| xan-km sheared gel in 0.15 M NaCl heated to 90° C. | | | xan-km sheared gel in 0.15 M NaCl heated to 70° C. | | | xan-km sheared gel (0.5% conc.) in 0.15 M NaCl heated to 50° C. | | |
|---|---|---|---|---|---|---|---|---|
| frequency Hz | G' Pa | G" Pa | frequency Hz | G' Pa | G" Pa | frequency Hz | G' Pa | G" Pa |
| 0.10 | 25.87 | 4.31 | 0.10 | 19.81 | 4.54 | 0.10 | 28.28 | 2.89 |
| 0.13 | 26.65 | 4.42 | 0.13 | 21.42 | 4.34 | 0.13 | 28.79 | 2.96 |
| 0.16 | 27.74 | 4.44 | 0.16 | 22.19 | 4.31 | 0.16 | 29.45 | 3.06 |
| 0.20 | 28.41 | 4.96 | 0.20 | 23.12 | 4.36 | 0.20 | 30.22 | 3.32 |
| 0.25 | 29.20 | 5.21 | 0.25 | 23.74 | 4.86 | 0.25 | 30.41 | 3.31 |
| 0.32 | 30.16 | 5.22 | 0.32 | 24.38 | 5.29 | 0.32 | 30.85 | 3.24 |
| 0.40 | 30.82 | 5.87 | 0.40 | 25.19 | 5.86 | 0.40 | 31.42 | 3.63 |
| 0.50 | 31.78 | 6.02 | 0.50 | 26.00 | 5.86 | 0.50 | 31.98 | 4.06 |
| 0.63 | 32.65 | 6.34 | 0.63 | 26.89 | 6.04 | 0.63 | 32.72 | 4.17 |
| 0.79 | 33.49 | 6.92 | 0.79 | 27.73 | 6.46 | 0.79 | 33.09 | 4.40 |

TABLE 18-continued

| xan-km sheared gel in 0.15 M NaCl heated to 90° C. | | | xan-km sheared gel in 0.15 M NaCl heated to 70° C. | | | xan-km sheared gel (0.5% conc.) in 0.15 M NaCl heated to 50° C. | | |
|---|---|---|---|---|---|---|---|---|
| frequency Hz | G' Pa | G" Pa | frequency Hz | G' Pa | G" Pa | frequency Hz | G' Pa | G" Pa |
| 1.00 | 34.48 | 7.14 | 1.00 | 28.67 | 6.93 | 1.00 | 33.78 | 4.70 |
| 1.26 | 35.49 | 7.69 | 1.26 | 29.53 | 7.43 | 1.26 | 34.15 | 5.09 |
| 1.58 | 36.71 | 8.19 | 1.58 | 30.41 | 8.15 | 1.58 | 34.86 | 5.45 |
| 2.00 | 37.92 | 8.75 | 2.00 | 31.43 | 8.62 | 2.00 | 35.54 | 5.96 |
| 2.52 | 38.79 | 9.19 | 2.52 | 32.59 | 8.90 | 2.52 | 35.66 | 6.16 |
| 3.15 | 39.88 | 9.78 | 3.15 | 33.75 | 9.56 | 3.15 | 36.17 | 6.93 |
| 3.99 | 40.70 | 10.22 | 3.99 | 34.75 | 9.86 | 3.99 | 35.83 | 7.76 |
| 5.00 | 41.90 | 10.99 | 5.00 | 35.52 | 10.79 | 5.00 | 36.13 | 8.25 |
| 6.29 | 42.61 | 11.71 | 6.29 | 36.55 | 11.24 | 6.29 | 35.64 | 8.76 |
| 7.93 | 44.20 | 12.49 | 7.93 | 38.09 | 12.02 | 7.93 | 35.32 | 9.42 |
| 10.01 | 46.49 | 13.19 | 10.01 | 40.04 | 12.71 | 10.01 | 35.14 | 10.40 |

TABLE 19

| xan-km sheared gel in 0.1 M ZnCl$_2$ heated to 90° C. | | | xan-km sheared gel in 0.1 M ZnCl$_2$ heated to 70° C. | | | xan-km sheared gel in 0.1 M ZnCl$_2$ heated to 50° C. | | |
|---|---|---|---|---|---|---|---|---|
| frequency Hz | G' Pa | G" Pa | frequency Hz | G' Pa | G" Pa | frequency Hz | G' Pa | G" Pa |
| 1.00 | 35.67 | 12.87 | 1.00 | 33.38 | 8.00 | 1.00 | 32.75 | 7.57 |
| 1.18 | 37.46 | 13.17 | 1.26 | 34.65 | 8.28 | 1.26 | 33.68 | 7.92 |
| 1.39 | 39.21 | 13.52 | 1.58 | 35.47 | 8.59 | 1.58 | 34.91 | 8.18 |
| 1.64 | 40.75 | 13.78 | 2.00 | 36.47 | 9.04 | 2.00 | 35.87 | 8.57 |
| 1.93 | 42.34 | 14.17 | 2.52 | 37.80 | 9.56 | 2.52 | 36.95 | 8.75 |
| 2.28 | 44.10 | 14.73 | 3.15 | 38.90 | 10.10 | 3.15 | 38.01 | 8.97 |
| 2.68 | 46.19 | 15.11 | 3.99 | 39.65 | 10.08 | 3.99 | 39.03 | 9.63 |
| 3.15 | 47.86 | 15.55 | 5.00 | 40.00 | 11.02 | 5.00 | 39.29 | 9.83 |
| 3.72 | 49.10 | 16.08 | 6.29 | 40.77 | 11.17 | 6.29 | 40.28 | 9.99 |
| 4.39 | 50.69 | 16.47 | 7.93 | 41.38 | 11.68 | 7.93 | 40.98 | 10.21 |
| 5.17 | 51.80 | 16.73 | 10.01 | 42.26 | 12.40 | 10.01 | 42.62 | 10.63 |
| 6.10 | 52.82 | 17.04 | | | | | | |
| 7.18 | 53.88 | 17.01 | | | | | | |
| 8.48 | 54.98 | 17.46 | | | | | | |
| 10.01 | 55.93 | 17.91 | | | | | | |

The following examples illustrate formulations in which gels of the present invention can be used:

The gel used in these formulation examples was provided in the form of a powder containing xanthan gum, locust bean gum, konjac mannan gum and sodium chloride.

The powder was incorporated in the aqueous phase of the formulation. The aqueous phase was heated to at least 80° C. until fully hydrated, thoroughly mixed and then cooled with constant stirring to below 35° C. A gel of the invention was thereby formed in situ in the composition.

Formulation Example 1—Bath Gel (1)

| | Sample 1 % w/w | Sample 2 % w/w |
|---|---|---|
| Sodium laureth sulfate | 46.5 | 46.3 |
| Disodium pareth-3 sulfosuccinate | 25 | 25 |
| Lauric fatty acids | 11.5 | 11.5 |
| Diethanolamine | 11.5 | 11.5 |
| Methyl gluceth-10 ethoxylated | 2.5 | 2.5 |
| Laneth-16 | 3 | 3 |
| Gel of the invention | — | 0.3 |
| Preservative | q.s | q.s |
| Parfum | q.s | q.s |

Method:

Stage 1

The following materials were added to water in order using stirring: Sodium laureth sulfate, Disodium pareth sulfosuccinate, lauric fatty acids, diethanolamine, methyl gluceth-10, laneth-16 (and gel of the invention in sample 2).

Stage 2

Maintaining the stirring, the bulk was heated to 80° C. when uniform, the bulk was cooled with constant stirring to below 35° C.

Stage 3

The preservative and perfume were added and the product was made to weight with purified water. The product was stirred until cool and uniform.

Advantages of using a gel of the invention:

Stable, reproducible viscosity build.
Improves the pouring, causing no drips.
Improves textural properties.
Results in a conditioned end feel.

Formulation Example 2—Bath Gel (2)

| | Sample 1 % w/w | Sample 2 % w/w |
|---|---|---|
| Aqua | 76 | 75.8 |
| Sodium lauryl sulfate | 20 | 20 |
| Cocamidopropyl betaine | 1.5 | 1.5 |
| Sodium chloride | 0.2 | 0.2 |
| PEG-6 Cocamide | 1 | 1 |
| Dipropylene glycol | 0.25 | 0.25 |
| PEG-18 glyceryl oleate/cocoate | 0.5 | 0.5 |
| Gel of the invention | — | 0.2 |
| Preservative | q.s | q.s |
| Parfum | q.s | q.s |

Method:

Stage 1

The following materials were added to the water in order using stirring: Sodium lauryl sulfate, sodium chloride, PEG-6 cocamide, dipropylene glycol, PEG-18, cocamidopropyl betaine (and gel of the invention in sample 2).

Stage 2

Maintaining stirring, the bulk was heated to 80° C. Once uniform, the bulk was cooled with constant stirring to below 35° C.

Stage 3

The preservative and perfume were added and the product was made to weight with purified water. The product was stirred until cool and uniform.

Advantages of using a gel of the invention:

Stable, reproducible viscosity build.
Improves the pouring, causing no drips.
Improves textural properties.
Results in a conditioned end feel.

Formulation Example 3—Shower Gel (1)

|  | Sample 1 % w/w | Sample 2 % w/w |
| --- | --- | --- |
| Aqua | 77.5 | 77.3 |
| Sodium lauryl sulfate | 10.5 | 10.5 |
| Cocoamphocarboxypropionate | 6 | 6 |
| Sodium lauroyl sarcosinate | 3 | 3 |
| Cocamide MEA | 3 | 3 |
| Gel of the invention | — | 0.2 |
| Preservative | q.s | q.s |
| Parfum | q.s | q.s |

Method:
Stage 1

The following materials were added to the water in order with stirring: Sodium lauryl sulfate, cocoamphocarboxypropionate, sodium lauroyl sarcosinate, cocamide MEA (and gel of the invention in sample 2).

Stage 2

Maintaining stirring, the bulk was heated to 80° C. Once uniform, the bulk was cooled with constant stirring to below 35° C.

Stage 3

The preservative and perfume were added and the product was made to weight with purified water. The product was stirred until cool and uniform.

Advantages of using a gel of the invention:

Stable, reproducible viscosity build.

Improves the pouring, causing no drips.

Rheology modifier.

Improves textural properties.

Results in a conditioned end feel.

Formulation Example 4—Shower Gel (2)

|  | Sample 1 % w/w | Sample 2 % w/w |
| --- | --- | --- |
| Aqua | 75.5 | 75.3 |
| Sodium lauryl sulfate | 20 | 20 |
| Cocamidopropyl betaine | 1.5 | 1.5 |
| Sodium chloride | 0.2 | 0.2 |
| PEG-6 Cocamide | 1 | 1 |
| Dipropylene glycol | 0.25 | 0.25 |
| PEG-18 glyceryl oleate/cocoate | 0.5 | 0.5 |
| PEG-40 hydrogenated castor oil | 0.5 | 0.5 |
| Polyquaternium-7 | 0.04 | — |
| PEG-7 glyceryl cocoate | 0.5 | 0.5 |
| Tetrasodium EDTA | 0.02 | 0.02 |
| Gel of the invention | — | 0.2 |
| Preservative | q.s | q.s |
| Parfum | q.s | q.s |

Method:
Stage 1

The following materials were added to the water in order with stirring: (in sample 1, polyquaternium-7 was added first) Tetrasodium EDTA, Sodium lauryl sulfate, sodium chloride, PEG-6, dipropylene glycol, PEG-18, PEG-40, PEG-7, cocamidopropyl betaine (and gel of the invention in sample 2).

Stage 2

Maintaining stirring, the bulk was heated to 80° C. Once uniform, the bulk was cooled with constant stirring to below 35° C.

Stage 3

The preservative and perfume were added and the product was made to weight with purified water. The product was stirred until cool and uniform.

Advantages of using a gel of the invention:

Stable, reproducible viscosity build.

Improves the pouring, causing no drips.

Rheology modifier.

Improves textural properties.

Skin conditioning effect.

Results in a conditioned end feel.

Formulation Example 5—Shampoo (1)

|  | Sample 1 % w/w | Sample 2 % w/w |
| --- | --- | --- |
| Aqua | 84.86 | 84.64 |
| Ammonium lauryl sulfate | 5.04 | 5.04 |
| Lauroyl sarcosine | 5 | 5 |
| Lauramide DEA | 5 | 5 |
| Tetrasodium EDTA | 0.1 | 0.1 |
| Gel of the invention | — | 0.2 |
| Preservative | q.s | q.s |
| Parfum | q.s | q.s |

Method:
Stage 1

The following materials were added to the water in order with stirring: Tetrasodium EDTA, Ammonium lauryl sulfate, lauroyl sarcosinate, lauramide DEA (and gel of the invention in sample 2).

Stage 2

Maintaining stirring, the bulk was heated to 80° C. Once uniform, the bulk was cooled with constant stirring to below 35° C.

Stage 3

The preservative and perfume were added and the product was made to weight with purified water. The product was stirred until cool and uniform.

Advantages of using a gel of the invention:

Stable, reproducible viscosity build.

Improves the pouring, causing no drips.

Rheology modifier.

Soft hair-feel effect.

Improves textural properties.

Results in a conditioned end feel.

Formulation Example 6—Shampoo (2)

|  | Sample 1 % w/w | Sample 2 % w/w |
| --- | --- | --- |
| Aqua | 87.5 | 87.3 |
| Sodium lauryl sulfate | 7.8 | 7.8 |
| Sodium chloride | 0.8 | 0.8 |
| Cocamidopropyl betaine | 0.75 | 0.75 |
| Glycol disterate | 0.8 | 0.8 |
| Laureth-3 | 2 | 2 |
| Gel of the invention | — | 0.2 |
| Preservative | q.s | q.s |
| Parfum | q.s | q.s |

Method:

Stage 1

The following materials were added to the water in order with stirring: Sodium lauryl sulfate, sodium chloride, laureth-3, cocamidopropyl betaine (and gel of the invention in sample 2).

Stage 2

Maintaining stirring, the bulk was heated to 80° C. Glycol distearate was then added and dispersed. Once uniform, the bulk was cooled with constant stirring to below 35° C.

Stage 3

The preservative and perfume were added and the product was made to weight with purified water. The product was stirred until cool and uniform and the pearl had set up.

Advantages of using a gel of the invention:
Stable, reproducible viscosity build.
Improves the pouring, causing no drips.
Rheology modifier.
Soft hair-feel effect.
Pearl stabiliser.
Improves textural properties.
Results in a conditioned end feel.

Formulation Example 7—Shampoo and Conditioner 2-in-1 (1)

|  | Sample 1 % w/w | Sample 2 % w/w |
| --- | --- | --- |
| Aqua | 67.9 | 67.6 |
| Alpha olefin sulfonate | 25 | 25 |
| Cocamide DEA | 2 | 2 |
| Lauramide DEA | 1 | 1 |
| Oleamide MIPA | 1.5 | 1.5 |
| Cocamidopropyl betaine | 2 | 2 |
| Oleth-3 phosphate | 0.1 | 0.1 |
| Lauric acid | 0.25 | 0.25 |
| Sodium chloride | 0.25 | 0.25 |
| Gel of the invention | — | 0.3 |
| Preservative | q.s | q.s |
| Parfum | q.s | q.s |

Method:

Stage 1

The following materials were added to the water in order with stirring: Alpha olefin sulfonate, cocamide DEA, lauramide DEA, oleamide MIPA, cocamidopropyl betaine, lauric acid; oleth-3 phosphate (and Gel of the invention in sample 2).

Stage 2

Maintaining stirring, the bulk was heated to 80° C. Once uniform, the bulk was cooled with constant stirring to below 35° C.

Stage 3

The preservative and perfume were added and the product was made to weight with purified water. The product was stirred until cool and uniform.

Advantages of using a gel of the invention:
Stable, reproducible viscosity build.
Improves the pouring, causing no drips.
Rheology modifier.
Soft hair-feel effect.
Stabiliser.
Improves textural properties.
Results in a conditioned end feel.

Formulation Example 8—Shampoo and Conditioner 2-in-1 (2)

|  | Sample 1 % w/w | Sample 2 % w/w |
| --- | --- | --- |
| Aqua | 83 | 83.1 |
| Sodium lauryl sulfate | 8 | 8 |
| Cocamidopropyl betaine | 2 | 2 |
| Ethylene glycol monostearate | 3 | 3 |
| Dimethicone | 3.5 | 3.5 |
| Hydroxypropyl guar hydroxypropyltrimonium chloride | 0.4 | — |
| Citric acid | 0.02 | 0.02 |
| Tetrasodium EDTA | 0.05 | 0.05 |
| Gel of the invention | — | 0.3 |
| Preservative | q.s | q.s |
| Parfum | q.s | q.s |

Method:

Stage 1

The following materials were added to the water in order with stirring: (hydroxypropyl guar in was added first in sample 1) Citric acid, Tetrasodium EDTA, sodium lauryl sulfates cocamidopropyl betaine, ethylene glycol monostearate (and gel of the invention in sample 2).

Stage 2

Maintaining stirring, the bulk was heated to 75° C. Once uniform, dimethicone was added and dispersed. The bulk was then cooled with constant stirring to below 35° C.

Stage 3

The preservative and perfume were added and the product was made to weight with purified water. The product was stirred until cool and uniform.

Advantages of using a gel of the invention:
Stable, reproducible viscosity build.
Improves the pouring, causing no drips.
Rheology modifier.
Soft hair-feel effect.
Stabilises dimethicone emulsion.
Improves textural properties.
Results in a conditioned end feel.

Formulation Example 9—Anti-dandruff Shampoo (1)

|  | Sample 1 % w/w | Sample 2 % w/w |
| --- | --- | --- |
| Aqua | 77.35 | 76.95 |
| Sodium N-methyl-N-myristoyl-taurate | 13.65 | 13.65 |
| Laneth-10 acetate | 1 | 1 |
| Coconut oil diethanolamine condensate | 5 | 5 |
| Zinc pyrithione (dispersion) | 2 | 2 |
| Gel of the invention | — | 0.4 |
| Preservative | q.s | q.s |
| Parfum | q.s | q.s |

Method:

Stage 1

The following materials were added to the water in order with stirring: Sodium methyl myristoyl taurate, laneth-10, coconut oil, zinc pyrithione dispersion (and gel of the invention in sample 2).

Stage 2

Maintaining stirring, the bulk was heated to 80° C. Once uniform, the bulk was cooled with constant stirring to below 35° C.

Stage 3

The preservative and perfume were added and the product was made to weight with purified water. The product was stirred until cool and uniform.

Advantages of using a gel of the invention:
Stable, reproducible viscosity build.
Improves the pouring, causing no drips.
Rheology modifier.
Soft hair-feel effect.
Suspension of Zinc Pyrithione.
Aids deposition.
Improves textural properties.
Results in a conditioned end feel.

Formulation Example 10—Anti-dandruff Shampoo (2)

| | Sample 1 % w/w | Sample 2 % w/w |
|---|---|---|
| Aqua | 83 | 83 |
| Sodium lauryl sulfate | 8 | 8 |
| Cocamidopropyl betaine | 2 | 2 |
| Ethylene glycol monostearate | 3 | 3 |
| Dimethicone | 3.5 | 3.5 |
| Hydroxypropyl guar hydroxypropyltrimonium chloride | 0.4 | — |
| Citric acid | 0.02 | 0.02 |
| Tetrasodium EDTA | 0.05 | 0.05 |
| Zinc pyrithione (dispersion) | 1 | 1 |
| Gel of the invention | — | 0.4 |
| Preservative | q.s | q.s |
| Parfum | q.s | q.s |

Method:

Stage 1

The following materials were added to the water in order with stirring: (hydroxypropyl guar in was added first in sample 1) Citric acid, Tetrasodium EDTA, sodium lauryl sulfate, cocamidopropyl betaine, ethylene glycol monostearate, zinc pyrithione dispersion (and gel of the invention in sample 2).

Stage 2

Maintaining stirring, the bulk was heated to 75° C. Once uniform, dimethicone was added and dispersed. The bulk was then cooled with constant stirring to below 35° C.

Stage 3

The preservative and perfume were added and the product was made to weight with purified water. The product was stirred until cool and uniform.

Advantages of using a gel of the invention:
Stable, reproducible viscosity build.
Improves the pouring, causing no drips.
Rheology modifier.
Soft hair-feel effect.
Stabilises dimethicone emulsion.
Suspends zinc pyrithione.
Improves textural properties.
Results in a conditioned end feel.

Formulation Example 11—Liquid Soap

| | Sample 1 % w/w | Sample 2 % w/w |
|---|---|---|
| Aqua | 83.7 | 84.4 |
| Magnesium aluminium silicate | 1 | — |
| Potassium hydroxide | 2 | 2 |
| Propylene glycol | 2.5 | 2.5 |
| Sodium laureth sulfate | 1.8 | 1.8 |
| Oleic acid | 9 | 9 |
| Gel of the invention | — | 0.3 |
| Preservative | q.s | q.s |
| Parfum | q.s | q.s |

Method:

Stage 1

In sample 1, magnesium aluminium silicate was added to the water and dispersed using stirring. In both samples, potassium hydroxide was added and dispersed. Propylene glycol, sodium laureth sulfate and oleic acid were then added (and gel of the invention in sample 2).

Stage 2

Maintaining the stirring, the bulk was heated to 75° C., giving enough time for the oleic acid to saponify. The bulk was then cooled with constant stirring to below 35° C.

Stage 3

The preservative and perfume were added and the product was made to weight with purified water. The product was stirred until cool and uniform.

Advantages of using a gel of the invention:
Stable, reproducible viscosity build.
Rheology modifier.
Skin conditioning effect.
Stabilises the pearl.
Improves textural properties.
Results in a conditioned end feel.

Formulation Example 12—Beaded Shower Gel

| | Sample 1 % w/w | Sample 2 % w/w |
|---|---|---|
| Aqua | 77 | 82.6 |
| Sodium lauryl sulfate | 9.5 | 9.5 |
| Citric acid | 0.02 | 0.02 |
| Tetrasodium EDTA | 0.05 | 0.05 |
| Mica | 0.1 | 0.1 |
| Acrylates copolymer | 6 | — |
| PEG-40 hydrogenated castor oil | 0.5 | 0.5 |
| PEG-6 Cocamide | 1 | 1 |
| Dipropylene glycol | 0.25 | 0.25 |
| PEG-18 glyceryl oleate/cocoate | 0.5 | 0.5 |
| Gel of the invention | — | 0.4 |
| Preservative | q.s | q.s |
| Parfum | q.s | q.s |

Method:

Stage 1

The following materials were added to the water in order with stirring: Citric acid, Tetrasodium EDTA, sodium lauryl sulfate, PEG-40, PEG-6, PEG-18, (acrylates copolymer in sample 1) and dipropylene glycol (and gel of the invention in sample 2).

Stage 2

Maintaining stirring, the bulk was heated to 80° C. Once uniform, the bulk was then cooled with constant stirring to below 35° C.

Stage 3

The preservative, perfume and mica were added and the product was made to weight with purified water. The product was stirred until cool and uniform.

Advantages of using a gel of the invention:
Stable, reproducible viscosity build.
Improves the pouring, causing no drips.
Rheology modifier.
Skin conditioning effect.
Suspending beads.
Improves textural properties.
Results in a conditioned end feel.

Formulation Example 13—Oil-in-water Emulsion (1)

|  | Sample 1 % w/w | Sample 2 % w/w |
| --- | --- | --- |
| Aqua | 63 | 63 |
| Carbomer 940 | 0.35 | — |
| 1,3-Butylene glycol | 2 | 2 |
| Tetrasodium EDTA | 0.05 | 0.05 |
| Potassium Hydroxide | 0.06 | 0.06 |
| Polysorbate 80 | 1 | 1 |
| Paraffinum liquidum | 18 | 18 |
| Gel of the invention | — | 0.35 |
| Preservative | q.s | q.s |

Method:

Stage 1

EDTA was dispersed in the water using stirring. For sample 1, the Carbomer was then added and hydrated using homogenisation for 30 minutes. For sample 2, the gel of the invention was added and dispersed using stirring. Butylene glycol and Polysorbate 80 were then added and mixed until uniform using stirring. This phase was then heated to 80° C.

Stage 2

The paraffinum liquidum was weighed into a separate vessel and heated to 70° C.

Stage 3

The oil phase was added to the aqueous phase and an emulsion was formed using high shear homogenisation for 10 minutes. The Potassium Hydroxide was then added and the shear was maintained for a further 5 minutes.

Stage 4

The emulsion was cooled to below 35° C. using stirring. The preservative was then added and the product was made to weight with purified water. The emulsion was stirred until cool and uniform.

Advantages of using a gel of the invention:
Stable, reproducible viscosity build.
Rheology modifier.
Emulsion stabiliser.
Improves textural properties.
Skin conditioning effect.
Results in a conditional end feel.

Formulation Example 14—Oil-in-water Emulsion (2)

|  | Sample 1 % w/w | Sample 2 % w/w |
| --- | --- | --- |
| Aqua | 77 | 77 |
| Glycerin | 5 | 5 |
| Paraffinium liquidum | 5 | 5 |
| Dicaprylyl maleate | 3 | 3 |

-continued

|  | Sample 1 % w/w | Sample 2 % w/w |
| --- | --- | --- |
| Petrolatum | 3 | 3 |
| Cetyl alcohol | 2 | 2 |
| Steareth-2 | 1.5 | 1.5 |
| Glyceryl stearate | 1.5 | 1.5 |
| Steareth-21 | 1 | 1 |
| Sodium citrat | 0.06 | 0.06 |
| Citric acid | 0.02 | 0.02 |
| Hydroxyethyl cellulose | 0.3 | — |
| Tetrasodium EDTA | 0.05 | 0.05 |
| Gel of the invention | — | 0.3 |
| Preservative | q.s | q.s |
| Parfum | q.s | q.s |

Method:

Stage 1

EDTA, citric acid, sodium citrate and glycerin were dispersed in the water using stirring. For sample 1, the hydroxyethyl cellulose was then added and hydrated using homogenisation for 5 minutes. For sample 2, the gel of the invention was added and dispersed with stirring. This phase was then heated to 80° C.

Stage 2

The oils and waxes were mixed in a separate vessel and heated to 70° C. until melted.

Stage 3

The oil phase was added to the aqueous phase and an emulsion was formed using high shear homogenisation for 10 minutes.

Stage 4

The emulsion was cooled to below 35° C. using stirring. The preservative was then added and the product was made to weight with purified water. The emulsion was stirred until cool and uniform.

Advantages of using a gel of the invention:
Stable, reproducible viscosity build.
Rheology modifier.
Skin conditioning effect.
Emulsion stabiliser.
Improves textural properties.
Results in a conditioned end feel.

Formulation Example 15—Water-in-oil Emulsion

|  | Sample 1 % w/w | Sample 2 % w/w |
| --- | --- | --- |
| Aqua | 76.93 | 76.73 |
| 1,3-Butylene glycol | 5 | 5 |
| Sodium chloride | 1 | 1 |
| Cetyl dimethicone copolyol | 1.5 | 1.5 |
| Sorbitan isostearate | 0.5 | 0.5 |
| Stearic acid | 0.05 | 0.05 |
| Paraffinum liquidum | 15 | 15 |
| Butylated hydroxytoluene | 0.02 | 0.02 |
| Gel of the invention | — | 0.2 |
| Preservative | q.s | q.s |

Method:

Stage 1

Sodium chloride, butylene glycol (and gel of the invention in sample 2) were added to the water using stirring. This phase was heated to 80° C. maintaining stirring.

Stage 2

The oil phase was mixed and heated to 70° C. until melted and uniform.

Stage 3

Using high speed stiring, the aqueous phase was slowly added to the oil phase and stirred until emulsified and uniform. The emulsion was then transferred to a homogeniser and high shear was applied for 5 minutes.

Stage 4

The emulsion was cooled to below 35° C. with stirring and the preservative was added. Stirring continued until cool and uniform.

Advantages of using a gel of the invention:
Improves textural properties.
Results in a conditioned end feel.

Formulation Example 16—Cold Cream

|  | Sample 1 % w/w | Sample 2 % w/w |
| --- | --- | --- |
| Aqua | 69 | 68.7 |
| Magnesium aluminium silicate | 1 | — |
| Synthetic beeswax | 1.5 | 1.5 |
| Fatty acid ester | 1.5 | 1.5 |
| Paraffinum liquidum | 20 | 20 |
| Sorbitan monopalmitate fatty acid ester | 3.5 | 3.5 |
| Polysorbate 60 | 3.5 | 3.5 |
| Gel of the invention | — | 0.3 |
| Preservative | q.s | q.s |

Method:

Stage 1

In sample 1, magnesium aluminium silicate was added to the water and dispersed using stirring, followed by the addition and dispersion of polysorbate 60. In sample 2, the gel of the invention was added and dispersed using stirring. This phase was heated to 80° C. maintaining stirring.

Stage 2

The oil phase was mixed in a separate vessel and heated to 70° C. until melted and uniform.

Stage 3

Maintaining the temperature of both phases, the oil phase was added to the aqueous phase and an emulsion was formed using high shear homogenisation for 10 minutes.

Stage 4

The emulsion was cooled to below 35° C. using stirring. The preservative was then added and the product was made to weight with purified water. The emulsion was stirred until cool and uniform.

Advantages of using a gel of the invention:
Stable, reproducible viscosity build.
Rheology modifier.
Emulsion stabiliser.
Improves textural properties.
Skin conditioning effect resulting in a conditioned end feel.

Formulation Example 17—Anti-perspirant Stick

|  | Sample 1 % w/w | Sample 2 % w/w |
| --- | --- | --- |
| Aqua | 32.5 | 32.2 |
| Stearic acid | 6 | 6 |
| Sorbitol | 2.8 | 2.8 |
| Sodium aluminium chlorhydroxylactate | 18 | 18 |
| Sodium hydroxide | 0.7 | 0.7 |
| Ethanol | 40 | 40 |
| Gel of the invention | — | 0.3 |

Method:

Stage 1

Into the water, stearic acid, sorbitol (and gel of the invention in sample 2) were added. Sodium hydroxide was then added with stirring. This was heated to 80° C. until uniform, and giving the stearic acid sufficient time to saponify. The sodium aluminium chlorhydroxylacetate was added and dispersed with stirring.

Stage 2

The bulk was cooled to 50° C. with stirring. At this temperature, the ethanol was added and dispersed with stirring. The cooling continued until the bulk was at ambient temperature.

This product was packed into solvent sealed cases.

Advantages of using a gel of the invention:
Sodium stearate crystal structure modifier.
Rheology modifier.
Moisture absorption properties.
Improves textural properties.
Results in a conditioned end feel.

Formulation Example 18—Body Lotion

|  | Sample 1 % w/w | Sample 2 % w/w |
| --- | --- | --- |
| Aqua | 68.47 | 68.47 |
| Carbomer 940 | 0.3 | — |
| Sodium hydroxide | 0.028 | 0.028 |
| Glycerine | 5 | 5 |
| Glyceryl monostearate and polyoxyethylene | 4 | 4 |
| Stearate fatty acid ester | 2 | 2 |
| Paraffinum liquidum | 15 | 15 |
| Cholesterol | 5 | 5 |
| Oleyl alcohol | 2 | 2 |
| Tetrasodium EDTA | 0.05 | 0.05 |
| Gel of the invention | — | 0.3 |
| Preservative | q.s | q.s |

Method:

Stage 1

EDTA was dispersed in the water using stirring. For sample 1, the Carbomer was then added and hydrated using homogenisation for 30 minutes. For sample 2, the gel of the invention was added and dispersed using stirring. Glycerin was then added and stirred until uniform using stirring. This phase was then heated to 80° C.

Stage 2

The oil phase was mixed in a separate vessel and heated to 70° C. until melted and uniform.

Stage 3

The oil phase was added to the aqueous phase and an emulsion was formed using high shear homogenisation for 10 minutes. Sodium hydroxide was then added and the shear was maintained for a further 5 minutes.

Stage 4

The emulsion was cooled to below 35° C. using stirring. The preservative was then added and the product was made to weight with purified water. The emulsion was stirred until cool and uniform.

Advantages of using a gel of the invention:
Stable, reproducible viscosity build.
Rheology modifier.
Emulsion stabiliser.
Improves textural properties.
Skin conditioning effect.
Results in a conditioned end feel.

Formulation Example 19—Hair Conditioner (1)

|  | Sample 1 % w/w | Sample 2 % w/w |
|---|---|---|
| Aqua | 89.8 | 89.5 |
| Cetyl trimethyl ammonium chloride | 1.5 | 1.5 |
| Alumina | 0.5 | 0.5 |
| Petrolatum | 1.5 | 1.5 |
| Glyceryl stearate | 0.2 | 0.2 |
| Acetylated lanolin alcohol | 2 | 2 |
| Mineral oil (and) lanolin alcohol | 2 | 2 |
| Stearyl alcohol | 2.5 | 2.5 |
| Gel of the invention | — | 0.3 |
| Preservative | q.s | q.s |
| Parfum | q.s | q.s |

Method:
Stage 1

The materials were added to the water in the order shown above (excluding the parfum and preservative) with stirring. Gel of the invention was added at this stage in sample 2. With constant stirring, the bulk was heated to 80° C. until all materials were dispersed, melted and uniform.

Stage 2

The product was cooled to below 35° C. using stirring. The preservative was then added and the product was made to weight with purified water. The product was then stirred until cool and uniform.

Advantages of using a gel of the invention:
Stabiliser
Conditioning agent
Rheology modifier
Deposition aid
Improves textural properties
Results in a conditioned end feel.

Formulation Example 20—Hair Conditioner (2)

|  | Sample 1 % w/w | Sample 2 % w/w |
|---|---|---|
| Aqua | 90 | 90.1 |
| Cetyl alcohol | 4 | 4 |
| Cocamide MEA | 2 | 2 |
| Stearamidopropyl dimethylamine | 1 | 1 |
| Centrimonium chloride | 0.5 | 0.5 |
| Citric acid | 0.02 | 0.02 |
| Lactic acid | 0.4 | 0.4 |
| Hydroxyethyl cellulose | 0.5 | — |
| Tetrasodium EDTA | 0.05 | 0.05 |
| Gel of the invention | — | 0.4 |
| Preservative | q.s | q.s |
| Parfum | q.s | q.s |

Method:
Stage 1

EDTA, citric acid and lactic acid were added to the water and dispersed with stirring. In sample 1, the hydroxyethyl cellulose was added and hydrated using a homogeniser for 5 minutes. In sample 2, the gel of the invention was added with stirring. The other materials were added to the water in the order shown above (excluding the parfum and preservative) with stirring. With constant stirring, the bulk was heated to 80° C. until all materials were dispersed, melted and uniform.

Stage 2

The product was cooled to below 35° C. using stirring. The preservative was then added and the product was made to weight with purified water. The product was then stirred until cool and uniform.

Advantages of using a gel of the invention:
Stabiliser
Conditioning agent
Rheology modifier
Deposition aid
Improves textural properties
Results in a conditioned end feel.

Formulation Example 21—Fluid Foundation (1)

|  | Sample 1 % w/w | Sample 2 % w/w |
|---|---|---|
| Aqua | 61.5 | 61.6 |
| Carbomer 941 | 0.5 | — |
| Lanolin oil | 5 | 5 |
| Paraffinum liquidum | 3.5 | 3.5 |
| Stearyl alcohol (and) ceteareth-20 condensate | 3 | 3 |
| Triethanolamine | 0.5 | 0.5 |
| Ethanol | 26 | 26 |
| Tetrasodium EDTA | 0.02 | 0.02 |
| Gel of the invention | — | 0.4 |
| Pigments | q.s | q.s |
| Preservative | q.s | q.s |

Method:
Stage 1

EDTA was added to the water and dispersed with stirring. In sample 1, the Carbomer was added and hydrated using a homogeniser for 30 minutes. In sample 2, the gel of the invention was added with stirring.

This phase was then heated to 80° C.

Stage 2

The oil phase was mixed in a separate vessel and heated to 70° C. until melted and uniform.

Stage 3

The oil phase was added to the aqueous phase and an emulsion was formed using high shear homogenisation for 10 minutes. Sodium hydroxide was then added and the shear was maintained for a further 5 minutes. Maintaining the shear, the pigments were slowly added and dispersed. The emulsion was sheared until uniform.

Stage 4

The emulsion was then cooled to below 35° C. with stirring. The preservative was added and the product was made to weight with purified water.

Advantages of using a gel of the invention:
Dispersing aid for the pigments
Suspending the pigments
Emulsion stabiliser Rheology modifier
Improves textural properties
Results in a conditioned end feel.

Formulation Example 22—Fluid Foundation (2)

|  | Sample 1 % w/w | Sample 2 % w/w |
|---|---|---|
| Aqua | 72 | 72 |
| 1,3-butylene glycol | 8 | 8 |
| Glycerin | 5 | 5 |
| Xanthan gum | 0.2 | — |
| Paraffinum liquidum | 4 | 4 |
| Cetearyl alcohol | 2 | 2 |
| PEG-20 stearate | 0.5 | 0.5 |
| Cetyl alcohol | 0.5 | 0.5 |
| Petrolatum | 1 | 1 |
| Theobromo cacao | 1.5 | 1.5 |
| BHT | 0.02 | 0.02 |
| Dimethicone | 5 | 5 |
| Tetrasodium EDTA | 0.05 | 0.05 |
| Gel of the invention | — | 0.25 |
| Preservative | q.s | q.s |
| Pigments | q.s | q.s |

Method:

Stage 1

EDTA was added to the water and dispersed with stirring. In sample 1, the Xanthan gum was added with stirring (pre-dispersed in glycerin and butylene glycol). In sample 2, the gel of the invention was added with stirring, followed by glycerin and butylene glycol. This phase was then heated to 80° C.

Stage 2

The oil phase was mixed in a separate vessel and heated to 70° C. until melted and uniform.

Stage 3

The oil phase was added to the aqueous phase and an emulsion was formed using homogenisation for 10 minutes. Maintaining the shear, the pigments were slowly added and dispersed.

Stage 4

The emulsion was then cooled to below 35° C. with stirring. The preservative was added and the product was made to weight with purified water.

Advantages of using a gel of the invention:
Dispersing aid for the pigments
Suspending the pigments
Emulsion stabiliser
Rheology modifier
Improves textural properties
Results in a conditioned end feel.

Formulation Example 23—Cream Foundation (1)

|  | Sample 1 % w/w | Sample 2 % w/w |
|---|---|---|
| Aqua | 69.4 | 69.2 |
| Stearic acid | 20 | 20 |
| Lanolin | 1 | 1 |
| Polyoxypropylene 15 stearyl ether | 3 | 3 |
| Glycerol monostearate (and) polyoxyethylene Stearate fatty acid ester | 3 | 3 |
| Propylene glycol | 3 | 3 |

-continued

|  | Sample 1 % w/w | Sample 2 % w/w |
|---|---|---|
| Triethanolamine | 0.6 | 0.6 |
| Gel of the invention | — | 0.2 |
| Pigments | q.s | q.s |
| Preservative | q.s | q.s |

Method:

Stage 1

Into the water, propylene glycol (and gel of the invention in sample 2) was added with stirring. The remaining materials were added in sequential order (excluding the pigments and preservative).

This was then heated to 80° C. with stirring.

Stage 2

An emulsion was formed using high shear homogenisation for 10 minutes. Maintaining the shear, the pigments were slowly added and dispersed. The emulsion was sheared until uniform.

Stage 3

The emulsion was then cooled to below 35° C. with stirring. The preservative was added and the product was made to weight with purified water.

Advantages of using a gel of the invention:
Dispersing aid for the pigments
Suspending the pigments
Emulsion stabiliser
Rheology modifier
Improves textural properties
Results in a conditioned end feel.

Formulation Example 24—Cream Foundation (2)

|  | Sample 1 % w/w | Sample 2 % w/w |
|---|---|---|
| Aqua | 73.7 | 73.7 |
| 1,3-butylene glycol | 8 | 8 |
| Cetearyl isononanoate | 5 | 5 |
| Dimethicone | 3 | 3 |
| Glycerin | 2 | 2 |
| Silica | 1.5 | 1.5 |
| Caprylic/capric tryiglcerides | 1.5 | 1.5 |
| Paraffinum liquidum | 1.2 | 1.2 |
| Petrolatum | 1.6 | 1.6 |
| Cetearyl octanoate | 1 | 1 |
| Cetearyl alcohol | 1 | 1 |
| Talc | 0.8 | 0.8 |
| Glyceryl stearate | 0.8 | 0.8 |
| Lactic acid | 0.4 | 0.4 |
| Xanthan gum | 0.1 | — |
| Tetrasodium EDTA | 0.05 | 0.05 |
| Gel of the invention | — | 0.3 |
| Pigments | q.s | q.s |
| Preservative | q.s | q.s |

Method:

Stage 1

EDTA and Lactic acid were added to the water and dispersed with stirring. In sample 1, the Xanthan gum was added with stirring (pre-dispersed in glycerin and butylene glycol). In sample 2, the gel of the invention was added with stirring, followed by glycerin and butylene glycol. This phase was then heated to 80° C.

Stage 2

The oil phase was mixed in a separate vessel and heated to 70° C. until melted and uniform.

Stage 3

The oil phase was added to the aqueous phase and an emulsion was formed using high shear homogenisation for 10 minutes. Maintaining the shear, the pigments (together with the talc and silica) were slowly added and dispersed. The emulsion was sheared until uniform. The emulsion was then cooled to below 35° C. with stirring. The preservative was added and the product was made to weight with purified water.

Advantages of using a gel of the invention:
Dispersing aid for the pigments
Suspending the pigments
Emulsion stabiliser
Rheology modifier
Improves textural properties
Results in a conditioned end feel.

Formulation Example 25—Face Powder/Granules (1)

|  | Sample 1 % w/w | Sample 2 % w/w |
| --- | --- | --- |
| Aqua | 2.85 | 2.85 |
| Titanium Dioxide | 23 | 23 |
| Mica | 47 | 47 |
| Talc | 18 | 18 |
| Carboxymethyl cellulose | 0.4 | — |
| Sorbitol | 2 | 2 |
| Glyceryl monostearate | 1.75 | 1.75 |
| Lanolin | 5 | 5 |
| Gel of the invention | — | 0.4 |
| Pigments | q.s | q.s |
| Preservative | q.s | q.s |

Method:

Stage 1

Sorbitol was stirred into the water. Carboxymethyl cellulose (and gel of the invention in sample 2) was added to this with stirring. Lanolin and glyceryl stearate were added and this phase was heated to 80° C. until melted and uniform.

Stage 2

Using stirring Titanium dioxide, Mica, Talc and pigments were added and dispersed. A Diosna mixer could be used to aid the dispersion.

Stage 3

The product was cooled to 35° C. with stirring. The preservative was added and the product was made to weight with purified water.

Advantages of using a gel of the invention:
Deposition
Enhanced wear
Enhanced structure
Improves textural properties
Results in a conditioned end feel.

Formulation Example 26—Face Powder/Granules (2)

|  | Sample 1 % w/w | Sample 2 % w/w |
| --- | --- | --- |
| Aqua | 3.2 | 3.2 |
| Talc | 74 | 76 |
| Microcrystalline cellulose | 10 | 10 |
| Magnesium stearate | 6 | 6 |
| 1,3-butylene glycol | 6 | 6 |

-continued

|  | Sample 1 % w/w | Sample 2 % w/w |
| --- | --- | --- |
| Gel of the invention | — | 0.8 |
| Pigments | q.s | q.s |
| Preservative | q.s | q.s |

Method:

Stage 1

Microcrystalline cellulose (and gel of the invention in sample 2) was dispersed in butylene glycol. Magnesium stearate was added and this phase was heated to 80° C. with stirring.

Stage 2

Using stirring, Talc and pigments were added and dispersed. A Diosna mixer could be used to aid this dispersion.

Stage 3

The product was cooled to 35° C. with stirring. The preservative was added and the product was made to weight with purified water.

Advantages of using a gel of the invention:
Deposition
Enhanced wear
Enhanced structure
Improved textural properties
Results in a conditioned end feel.

Formulation Example 27—Toothpaste

|  | Sample 1 % w/w | Sample 2 % w/w |
| --- | --- | --- |
| Aqua | 47 | 47 |
| Sorbitol | 30 | 30 |
| Hydrated silica | 16 | 16 |
| Sodium lauryl sulfate | 1.2 | 1.2 |
| Cellulose gum | 0.85 | — |
| Sodium monofluorophosphate | 0.75 | 0.75 |
| Sodium saccharin | 0.25 | 0.25 |
| Sodium hydroxide | 0.2 | 0.2 |
| Gel of the invention | — | 0.4 |
| Glycerin | 3 | 3 |
| Triclosan | 0.3 | 0.3 |
| Flavour | q.s | q.s |
| Preservative | q.s | q.s |

Method:

Stage 1

The materials (excluding the flavour and preservative) were added to the water in order, with stirring (Triclosan was pre-dispersed in glycerin). This was heated to 80° C. maintaining stirring until uniform.

Stage 2

A fryma mixer was then used to generate a uniform paste. This was mixed for 10 minutes. The product was then cooled to 35° C. The preservative and flavour were added and the product was made to weight with purified water. The product was mixed until uniform.

Advantages of using a gel of the invention:
Stable, reproducible viscosity build.
Rheology modifier.
Enhanced mouth feel.
Stabiliser.
Increased dwell time in the mouth.
Enhanced delivery of Triclosan.
Improves textural properties Formulation Example 28—Toothgel

|  | Sample 1 % w/w | Sample 2 % w/w |
| --- | --- | --- |
| Aqua | 53 | 53 |
| Glycerin | 45 | 45 |
| Carbomer | 1 | — |
| PEG-40 hydrogenated castor oil | 0.2 | 0.2 |
| Sodium hydroxide | 0.25 | 0.25 |
| Sodium fluoride | 0.024 | 0.024 |
| Gel of the invention | — | 0.5 |
| Triclosan | 0.3 | 0.3 |
| Flavour | q.s | q.s |
| Preservative | q.s | q.s |

Method:
Stage 1
In sample 1, the Carbomer was added to the water and hydrated using homogenisation for 30 minutes. In sample 2, the gel of the invention was added to the water with stirring. The remaining materials (excluding the flavour and preservative) were added in order (the Triclosan was pre-dispersed in the glycerin). This was heated to 80° C. maintaining stirring until uniform.
Stage 2
A fryma mixer was then used to generate a uniform paste. This was mixed for 10 minutes. The product was then cooled to 35° C. The preservative and flavour were added and the product was made to weight with purified water. The product was mixed until uniform.

Advantages of using a gel of the invention:
Stable, reproducible viscosity build.
Rheology modifier.
Enhanced mouth feel.
Stabiliser.
Increased dwell time in the mouth.
Enhanced delivery of Triclosan.
Improves textural properties Formulation Example 29—Body Scrub

|  | Sample 1 % w/w | Sample 2 % w/w |
| --- | --- | --- |
| Aqua | 66 | 65.7 |
| Lauroamphodiacetate | 8 | 8 |
| Sodium lauryl sulfate | 6 | 6 |
| Hexylene glycol | 6 | 6 |
| PEG-40 castor oil | 4 | 4 |
| Polysorbate 80 | 1.5 | 1.5 |
| Cetyl acetate | 1 | 1 |
| Acetylated lanolin alcohol | 0.5 | 0.5 |
| Methyl gluceth-20 | 2 | 2 |
| Glycerin | 4 | 4 |
| Polyethylene | 1 | 1 |
| Gel of the invention | — | 0.3 |
| Parfum | q.s | q.s |
| Preservative | q.s | q.s |

Method:
Stage 1
The materials (excluding the parfum, preservative and polyethylene) were added to the water in order with stirring, including gel of the invention in sample 2. This was heated to 80° C., maintaining the stirring. The bulk was stirred until uniform.

Stage 2
Maintaining the stirring the product was cooled to 35° C. The parfum, preservative and polyethylene were added and the product was made to weight with purified water. The product was stirred until the polyethylene was evenly distributed and the product was uniform.

Advantages of using a gel of the invention:
Viscosity control
Rheology modifier
Skin conditioning effect
Stabiliser
Suspending the polyethylene beads
Improves textural properties
Results in a conditioned end feel.

Formulation Example 30—Face Mask(1)

|  | Sample 1 % w/w | Sample 2 % w/w |
| --- | --- | --- |
| Aqua | 80 | 84.5 |
| Kaolin | 15 | 10 |
| Ethanol | 5 | 5 |
| Glycerin | 5 | 5 |
| Gel of the invention | — | 0.5 |
| Parfum | q.s | q.s |
| Preservative | q.s | q.s |

Method:
Stage 1
Kaolin, glycerin (and Gel of the invention in sample 2) were added to the water with stirring. This was heated to 80° C. A Torrence mixer was used to generate a uniform mix.
Stage 2
The bulk was cooled to 35° C. and the remaining materials were added. The product was then made to weight with purified water and stirred until uniform.

Advantages of using a gel of the invention:
Film-forming
Rheology modifier
Improves textural properties
Skin conditioning effect resulting in improved Skin feel
Results in a conditioned end feel Formulation Example 31—Face Mask (2)

|  | Sample 1 % w/w | Sample 2 % w/w |
| --- | --- | --- |
| Aqua | 65.75 | 66.15 |
| Kaolin | 12.5 | 12.5 |
| Glycerin | 7 | 7 |
| Paraffinum liquidum | 5 | 5 |
| Caprylic/capric triglyceride | 2 | 2 |
| Talc | 1.5 | 1.5 |
| Cetyl alcohol | 2.25 | 2.25 |
| Petrolatum | 1.5 | 1.5 |
| Glyceryl stearate | 1.5 | 1.5 |
| Cellulose gum | 0.5 | — |
| Hydroxyethyl cellulose | 0.5 | — |
| Gel of the invention | — | 0.6 |
| Preservative | q.s | q.s |
| Parfum | q.s | q.s |

Method:

Stage 1

The following materials were added to the water with stirring: Kaolin, glycerin, (hydroxyethyl cellulose and cellulose gum in sample 1 and gel of the invention in sample 2). This was heated to 80° C., maintaining the stirring. A torrence mixer was used to generate a uniform mix.

Stage 2

The oil phase, with the talc was mixed in a separate vessel and heated to 70° C. until melted and uniform.

Stage 3

The oil phase was added to the aqueous phase and an emulsion was formed using 10 minutes homogenisation. The emulsion was then cooled to 35° C. with stirring.

Stage 4

The preservative and perfume were added and the product was made to weight with purified water and stirred until uniform.

Advantages of using a gel of the invention:
Film-forming
Rheology modifier
Improves textural properties
Results in a conditioned end feel.

Formulation Example 32—Inorganic Sunscreen Formula (1)

|  | Sample 1 % w/w | Sample 2 % w/w |
|---|---|---|
| Aqua | 60 | 59.8 |
| Cetyl dimethicone copolyol | 1.5 | 1.5 |
| Glyceryl oleate | 2 | 2 |
| Dimethicone | 3 | 3 |
| Isopropyl palmitate | 8 | 8 |
| Ceresin | 1 | 1 |
| Paraffinum liquidum | 4 | 4 |
| Dicaprylyl maleate | 6 | 6 |
| Titanium dioxide MT100T | 5 | 5 |
| 1,3-butylene glycol | 8 | 8 |
| Magnesium sulphate | 1 | 1 |
| Gel of the invention | — | 0.2 |
| Preservative | q.s | q.s |

Method:

Stage 1

Magnesium sulphate, butylene glycol (and gel of the invention in sample 2) were added to the water using stirring. This phase was heated to 80° C. maintaining stirring.

Stage 2

The oil phase was mixed and heated to 70° C. until melted and uniform. At 70° C. the titanium dioxide was added and dispersed using homogenisation.

Stage 3

Using stirring, the aqueous phase was slowly added to the oil phase and stirred until emulsified and uniform. The emulsion was then transferred to a homogeniser and high shear was applied for 5 minutes.

Stage 4

The emulsion was cooled to below 35° C. with stirring and the preservative was added. Stirring continued until cool and uniform.

Advantages of using a gel of the invention:
Wetting agent for the titanium dioxide
Improves textural properties.
Results in a conditioned end feel.

Formulation Example 33—Inorganic Sunscreen Formula (2)

|  | Sample 1 % w/w | Sample 2 % w/w |
|---|---|---|
| Aqua | 52 | 51.8 |
| Cetyl dimethicone copolyol | 1.5 | 1.5 |
| Glyceryl oleate | 2 | 2 |
| Dimethicone | 3 | 3 |
| Isopropyl palmitate | 8 | 8 |
| Ceresin | 1 | 1 |
| Paraffinum liquidum | 4 | 4 |
| Dicaprylyl maleate | 6 | 6 |
| Titanium dioxide MT100T | 3 | 3 |
| Zinc oxide (Nanox) | 10 | 10 |
| 1,3-butylene glycol | 8 | 8 |
| Magnesium sulphate | 1 | 1 |
| Gel of the invention | — | 0.2 |
| Preservative | q.s | q.s |

Method:

Stage 1

Magnesium sulphate, butylene glycol (and gel of the invention in sample 2) were added to the water using stirring. This phase was heated to 80° C. maintaining stirring.

Stage 2

The oil phase was mixed and heated to 70° C. until melted and uniform. At 70° C. the titanium dioxide and zinc oxide were added and dispersed using homogenisation.

Stage 3

Using stirring, the aqueous phase was slowly added to the oil phase and stirred until emulsified and uniform. The emulsion was then transferred to a homogeniser and high shear was applied for 5 minutes.

Stage 4

The emulsion was cooled to below 35° C. with stirring and the preservative was added. Stirring continued until cool and uniform.

Advantages of using a gel of the invention:
Wetting agent for the titanium dioxide
Improves textural properties
Results in a conditioned end feel.

Formulation Example 34—Pain Relief Syrup

|  | Sample 1 % w/w | Sample 2 % w/w |
|---|---|---|
| Aqua | 30 | 31 |
| Glycerin | 30 | 30 |
| Sorbitol | 35 | 35 |
| Microcrystalline cellulose | 2 | 2 |
| Hydroxyethylcellulose | 0.3 | — |
| Acetaminophen | 2 | 2 |
| Potassium acesulfame | 0.05 | 0.05 |
| Gel of the invention | — | 0.4 |
| Preservative | q.s | q.s |
| Flavour | q.s | q.s |

Method:

Stage 1

The following materials were added to the water with stirring: Glycerin, sorbitol, microcrystalline cellulose (hydroxyethylcellulose in sample 1 and gel of the invention in sample 2). This was heated to 80° C. with maintained stirring.

Stage 2

The bulk was then cooled to 35° C. with stirring. Acetaminophen, potassium acesulfame, preservative and flavourings were then added and the product was made to weight with purified water. The stirring continued until the active was evenly distributed and the product was uniform.

Advantages of using a gel of the invention:

Suspension of active

Viscosity control

Delivery of active

Improves textural properties

Formulation Example 35—Mouthwash

|  | Sample 1 % w/w | Sample 2 % w/w |
|---|---|---|
| Aqua | 81 | 81 |
| Ethanol | 5 | 5 |
| Glycerin | 8 | 8 |
| Sorbitol | 5 | 5 |
| Sodium saccharin | 0.025 | 0.025 |
| Sodium fluoride | 0.05 | 0.05 |
| Polysorbate 20 | 0.2 | 0.2 |
| PEG-40 hydrogenated castor oil | 0.15 | 0.15 |
| Gel of the invention | — | 0.1 |
| Preservative | q.s | q.s |
| Flavour | q.s | q.s |

Method:

Stage 1

Glycerin, sorbitol (and gel of the invention in sample 2) were added to the water with stirring. This was heated to 80° C., maintaining stirring.

Stage 2

The bulk was then cooled to 35° C. Sodium saccharin, sodium fluoride, polysorbate 20, PEG-40 and Ethanol were pre-mixed together and added to the bulk. The preservative and flavour were added and the product was made to weight with purified water. Stirring was maintained until the product was cool and uniform.

Advantages of using a gel of the invention:

Enhanced mouth feel

Increased dwell time

Enhanced delivery of actives

Formulation Example 36—Hair Gel

|  | Sample 1 % w/w | Sample 2 % w/w |
|---|---|---|
| Aqua | 99 | 99 |
| Carbomer 940 | 0.35 | — |
| Glycerin | 0.5 | 0.5 |
| Tetrasodium EDTA | 0.05 | 0.05 |
| Potassium Hydroxide | 0.06 | 0.06 |
| Gel of the invention | — | 0.35 |
| Preservative | q.s | q.s |

Method

Stage 1

EDTA was dispersed in the water using stirring. For sample 1, the Carbomer was then added and hydrated using homogenisation for 30 minutes. For example 2, the gel was added and dispersed using stirring.

Glycerin was then added and mixed until uniform using stirring. Sample 2 was then heated to 80° C. (sample 1 remained at room temperature).

Stage 2

Sample 2 was cooled to below 35° C. using stirring. The preservative was then added to both samples and they were made to weight with purified water. The gels were stirred until cool and uniform.

Advantages of using a gel of the invention

Stable, reproducible viscosity build.

Rheology modifier.

Hair conditioning effect.

Hair styling and hold

Improved textural properties.

Results in a conditioned end feel.

Formulation Example 37—Sun Lotion

|  | Sample 1 % w/w | Sample 2 % w/w |
|---|---|---|
| Aqua | 64.8 | 59.45 |
| Ethanol | 10 | 10 |
| Octyldodecanol | 8 | 8 |
| Glycerin | 5 | 5 |
| Octyl methoxycinnamate | — | 2 |
| Octocrylene | — | 1 |
| Hydrogenated coco-glycerides | 3 | 3 |
| Butyl methoxydibenzoylmethane | — | 2 |
| Drometrizole trisiloxane (Mexoryl XL) | 3 | 3 |
| Terephthalylidene dicamphor sulfonic acid (Mexoryl SX) | 3 | 3 |
| 4-methylbenzylidene camphor | 1 | 1 |
| C12–15 alcohols benzoate | 1 | 1 |
| Coco-glucoside | 1 | 1 |
| Theobromo cacao | 0.5 | 0.5 |
| Tocopheryl acetate | 0.2 | 0.2 |
| Gel of the invention | 0.35 | 0.35 |
| Preservative | q.s | q.s |
| Parfum | q.s | q.s |

Method

Stage 1

EDTA and glycerin were dispersed in the water using stirring. Gel of the invention was then added and dispersed using stirring. This phase was then heated to 80° C.

Stage 2

The oil phase was mixed, including the sunscreens and heated to 70° C.

Stage 3

With the temperature of both phases at 70° C., the oil phase was added to the aqueous phase and an emulsion was formed using high shear homogenisation for 10 minutes Stage 4

The emulsion was cooled to below 30° C. with stirring. Tocopheryl acetate, Ethanol, preservatives and perfume were all added with stirring. This emulsion was made to weight with purified water and cooled to room temperature.

Advantages of a gel of the present invention

Stable, reproducible viscosity build.

Rheology modifier.

Enhanced SPF efficacy.

Improved textural properties.

Formulation Example 38—Sun Spray Lotion

|  | Sample 1 % w/w | Sample 2 % w/w |
| --- | --- | --- |
| Aqua | 64.3 | 59.45 |
| Ethanol | 10 | 10 |
| Octyldodecanol | 8 | 8 |
| Glycerin | 5 | 5 |
| Octyl methoxycinnamate | — | 2 |
| Octocrylene | — | 1 |
| Hydrogenated coco-glycerides | 3 | 3 |
| Butyl methoxydibenzoylmethane | — | 2 |
| Drometrizole trisiloxane (Mexoryl XL) | 3 | 3 |
| Terephthalylidene dicamphor sulfonic acid (Mexoryl SX) | 3 | 3 |
| 4-methylbenzylidene camphor | 1 | 1 |
| C12–15 alcohols benzoate | 1 | 1 |
| Coco-glucoside | 1 | 1 |
| Tocopheryl acetate | 0.2 | 0.2 |
| Gel of the invention | 0.35 | 0.35 |
| Tetrasodium EDTA | 0.05 | 0.05 |
| Preservative | q.s | q.s |
| Parfum | q.s | q.s |

Method
Stage 1
EDTA and glycerin were dispersed in the water using stirring. Gel of the invention was then added and dispersed using stirring. This phase was then heated to 80° C.
Stage 2
The oil phase was mixed, including the sunscreens and heated to 70° C.
Stage 3
With the temperature of both phases at 70° C., the oil phase was added to the aqueous phase and an emulsion was formed using high shear homogenisation for 10 minutes
Stage 4
The emulsion was cooled to below 30° C. with stirring. Tocopheryl acetate, Ethanol, preservatives and perfume were all added with stirring. The emulsion was made to weight with purified water and cooled to room temperature.

Advantages of a gel of the present invention
Stable, reproducible viscosity build.
Rheology modifier.
Enhanced SPF efficacy.
Improved textural properties.

Formulation Example 39—Sustained Release Zinc and Vitamin C Tablets

|  | Sample 1 % w/w | Sample 2 % w/w |
| --- | --- | --- |
| Ascorbic acid | 66 | 66 |
| Xanthan gum | 10 | — |
| Gel of the invention | — | 10 |
| Sorbitol | 17.5 | 17.5 |
| Magnesium stearate | 1 | 1 |
| Zinc oxide | 5.5 | 5.5 |

Method
Stage 1
The powdered components of the gel of the invention were added to water, heated to over 65° C. and then cooled with stirring to 35° C.

Stage 2
The ingredients were passed through a 30 mesh sieve in order, blended together in a turbula and then compressed to form the tablet.

Advantages of a gel of the present invention
Sustained release of actives
Enhances delivery of actives
Improved tablet structure

The invention claimed is:

1. A fluid gel obtained by a process which comprises subjecting a solution consisting of a mixture of xanthan and konjac mannan and, optionally, an electrolyte in a solvent to shear while cooling the solution from a temperature above the gelation temperature of the mixture, to the gelation temperature and recovering the resulting continuous gel, wherein the solvent is selected from water, alcohols, ketones and mixtures thereof.

2. A gel according to claim 1 wherein the xanthan and konjac mannan are present in a weight ratio of from 1:10 to 10:1.

3. A process for producing a fluid gel, which process comprises subjecting a solution consisting of a mixture of xanthan and konjac mannan and, optionally, an electrolyte in a solvent to shear while cooling the solution from a temperature above the gelation temperature of the mixture, to gelation temperature and recovering the resulting continuous gel, wherein the solvent is selected from water, alcohols, ketones and mixtures thereof.

4. A process according to claim 3 which further comprises the preliminary step of heating the said mixture to a temperature above the gelation temperature of the mixture.

5. A process according to claim 3 wherein the solution consists of from 0.05 to 2% by weight of the mixture of xanthan and konjac mannan and a solvent.

6. A process according to claim 3 wherein the solution before cooling is at a temperature from just above the gelation temperature of the mixture to 95° C.

7. A process according to claim 3 wherein the solution is cooled to room temperature.

8. A process according to claim 3 which further comprises, in either order, (i) heating the xanthan and the konjac mannan to a temperature greater than or equal to the gelation temperature of the mixture and (ii) mixing the xanthan and the konjac mannan together.

9. A composition comprising:
(i) a fluid gel obtained by a process which comprises subjecting a solution comprising a mixture of xanthan and konjac mannan in a solvent to shear while cooling the solution from a temperature above the gelation temperature of the mixture, to gelation temperature and recovering the resulting continuous gel wherein the solvent is selected from water, alcohols, ketones and mixtures thereof; and
(ii) a cosmetically or pharmaceutically acceptable carrier, adjuvant or diluent.

10. A composition according to claim 9 which further comprises one or more of a pigment, a pharmaceutically active compound, a sunscreen active component, a silicone or derivative thereof, an inorganic salt or a solvent.

11. A composition according to claim 10 wherein one or more of the further components is added to the solution before subjecting the solution to shearing.

12. A composition according to claim 9 which takes the form of a topical, oral or mucosal contact gel or lotion, or a viscous fluid.

13. A composition according to claim 9 obtained by a process which comprises:
  (a) forming a mixture in solution comprising one or more cosmetically or pharmaceutically acceptable carriers, adjuvants or diluents and a mixture of xanthan and konjac mannan in a solvent which is selected from water, alcohols, ketones and mixtures thereof;
  (b) subjecting the mixture to shear while cooling it from a temperature above the gelation temperature of the mixture; to gelation temperature and
  (c) recovering the resulting cosmetic or pharmaceutical composition.

14. A process for producing a cosmetic or pharmaceutical composition which process comprises:
  (a) forming a mixture in solution comprising one or more cosmetically or pharmaceutically acceptable carriers, adjuvants or diluents and a mixture of xanthan and konjac mannan;
  (b) subjecting the aqueous phase to shear while cooling it from a temperature above the gelation temperature of the mixture; to gelation temperature and
  (c) recovering the resulting cosmetic or pharmaceutical composition.

15. A process according to claim 14 which further comprises the preliminary step of heating the mixture to a temperature above the gelation temperature of the mixture.

16. A process according to claim 14 wherein the solution comprises from 0.05% to 2% by weight of the mixture of xanthan and konjac mannan.

17. A process according to claim 14 wherein the solution before cooling is at a temperature from just above the gelation temperature of the mixture to 95° C.

18. A process according to any one of claims 14 to 17 wherein the solution is cooled to room temperature.

19. A process according to any one of claim 14 to 18 which further comprises, in either order:
  (i) heating the xanthan and the one or more cosmetically or pharmaceutically acceptable carrier adjuvant or diluent, and the konjac mannan in a solvent which is selected from water, alcohols, ketones and mixtures thereof to a temperature greater than or equal to the gelation temperature of the mixture; and
  (ii) mixing the xanthan, the one or more cosmetically or pharmaceutically acceptable carrier adjuvant or diluent, and the konjac mannan together.

20. A fluid gel produced by the process of claim 3.

21. A cosmetic composition comprising the gel of claim 1.

22. A pharmaceutical composition comprising the gel of claim 1.

23. A method of treating mucous tissues comprising applying a topical or mucosal contact gel or lotion comprising the gel of claim 1.

24. A method of ultrasound or ECG imaging a subject comprising topically applying to the area or areas to be imaged a gel or lotion comprising the gel of claim 1.

* * * * *